(12) United States Patent
Cheesman

(10) Patent No.: US 11,935,079 B2
(45) Date of Patent: Mar. 19, 2024

(54) CONDUCTING DIGITAL SURVEYS THAT COLLECT AND CONVERT BIOMETRIC DATA INTO SURVEY RESPONDENT CHARACTERISTICS

(71) Applicant: QUALTRICS, LLC, Provo, UT (US)

(72) Inventor: Larry Dean Cheesman, Provo, UT (US)

(73) Assignee: Qualtrics, LLC, Provo, UT (US)

( * ) Notice: Subject to any disclaimer, the term of this patent is extended or adjusted under 35 U.S.C. 154(b) by 72 days.

(21) Appl. No.: 17/228,412

(22) Filed: Apr. 12, 2021

(65) Prior Publication Data

US 2021/0248631 A1    Aug. 12, 2021

Related U.S. Application Data

(63) Continuation of application No. 15/582,180, filed on Apr. 28, 2017, now Pat. No. 10,977,674.

(51) Int. Cl.
*G06Q 30/0203* (2023.01)
*A61B 5/0205* (2006.01)
(Continued)

(52) U.S. Cl.
CPC ....... *G06Q 30/0203* (2013.01); *A61B 5/0205* (2013.01); *A61B 5/165* (2013.01);
(Continued)

(58) Field of Classification Search
CPC ................................................. G06Q 30/0203
See application file for complete search history.

(56) References Cited

U.S. PATENT DOCUMENTS 7,921,036 B1 *  4/2011  Sharma .............. G06Q 20/3674
                                                        705/52
9,852,599 B1 * 12/2017  Slavin ..................... A61B 7/04
(Continued)

FOREIGN PATENT DOCUMENTS

JP         2006085241 A      3/2006
KR    10-2014-0115153 A      9/2014
(Continued)

OTHER PUBLICATIONS

Examination Report as received in European application 17907846.4 dated Feb. 2, 2022.
(Continued)

*Primary Examiner* — Renae Feacher
(74) *Attorney, Agent, or Firm* — Keller Preece PLLC

(57) ABSTRACT

This disclosure covers systems and methods that administer a digital survey to respondents who interact with a biometric sensor to collect and convert biometric data into behavioral and physical characteristics of the respondents. In certain embodiments, by converting biometric data into respondent characteristics, the disclosed systems and methods identify various unwritten or nonverbal responses of survey respondents who respond to a digital survey or who interact with a display medium that captures survey data. To facilitate review of respondents' characteristics and responses, in some embodiments, the disclosed systems and methods further categorize the converted respondent characteristics within a response database for the digital survey.

20 Claims, 16 Drawing Sheets

(51) Int. Cl.
*A61B 5/16* (2006.01)
*G06V 40/70* (2022.01)
*A61B 5/021* (2006.01)
*A61B 5/024* (2006.01)
*A61B 5/08* (2006.01)
*G06Q 30/0217* (2023.01)

(52) U.S. Cl.
CPC .............. *G06V 40/70* (2022.01); *A61B 5/021* (2013.01); *A61B 5/024* (2013.01); *A61B 5/0816* (2013.01); *G06Q 30/0217* (2013.01)

(56) References Cited

U.S. PATENT DOCUMENTS

| | | | |
|---|---|---|---|
| 2004/0117250 A1 | 6/2004 | Lubow et al. | |
| 2005/0149405 A1 | 7/2005 | Barnett et al. | |
| 2007/0198432 A1 | 8/2007 | Pitroda et al. | |
| 2008/0065468 A1* | 3/2008 | Berg | G06Q 30/02 705/7.32 |
| 2008/0172261 A1 | 7/2008 | Albertson et al. | |
| 2009/0177528 A1 | 7/2009 | Wu et al. | |
| 2010/0004977 A1 | 1/2010 | Marci et al. | |
| 2010/0036670 A1 | 2/2010 | Hill et al. | |
| 2011/0176005 A1* | 7/2011 | Kaneko | G06Q 20/20 348/150 |
| 2012/0002848 A1* | 1/2012 | Hill | G16Z 99/00 382/118 |
| 2012/0253953 A1* | 10/2012 | Aziz | G06Q 20/405 705/16 |
| 2012/0289788 A1* | 11/2012 | Jain | A61B 5/165 702/19 |
| 2014/0298260 A1* | 10/2014 | Abowd | G06F 3/04842 715/810 |
| 2015/0046375 A1* | 2/2015 | Mandel | G06T 13/80 706/11 |
| 2016/0338642 A1* | 11/2016 | Parara | A61B 5/1112 |
| 2017/0098166 A1 | 4/2017 | Lau et al. | |
| 2018/0315063 A1 | 11/2018 | Cheesman | |

FOREIGN PATENT DOCUMENTS

| | | |
|---|---|---|
| WO | WO 2007/135796 A1 | 11/2007 |
| WO | WO 2018/200031 A1 | 11/2018 |

OTHER PUBLICATIONS

Examination Report as received in Australian application 2017410949 dated Feb. 23, 2022.
Extended European Search Report as received in European Application 17907846.4 dated Jul. 28, 2020.
International Search Report & Written Opinion as received in PCT/US2017/062320 dated Mar. 14, 2018.
Blasco, Jorge et al., "A Survey of Wearable Biometric Recognition Systems," ACM Computing Surveys, vol. 49., No. 3, Article 43, Sep. 2016.
U.S. Appl. No. 15/582,180, Mar. 14, 2019, Office Action.
U.S. Appl. No. 15/582,180, Oct. 11, 2019, Office Action.
U.S. Appl. No. 15/582,180, Mar. 6, 2020, Office Action.
U.S. Appl. No. 15/582,180, Sep. 18, 2020, Office Action.
U.S. Appl. No. 15/582,180, Dec. 16, 2020, Notice of Allowance.

* cited by examiner

CONDUCTING DIGITAL SURVEYS THAT COLLECT AND CONVERT BIOMETRIC DATA INTO SURVEY RESPONDENT CHARACTERISTICS

CROSS-REFERENCE TO RELATED APPLICATIONS

The present application is a continuation of U.S. application Ser. No. 15/582,180, filed on Apr. 28, 2017. The aforementioned application is hereby incorporated by reference in its entirety.

BACKGROUND

Digital content providers increasingly distribute digital surveys and other digital content to network users and other audiences. As digital content proliferates, audiences find both a seemingly endless amount of digital content competing for their attention and numerous computing devices that display that digital content. This increase in both digital content and computing devices complicates the administration of digital surveys, whether that survey be digitally distributed through personal computing devices or passively taken by audiences engaging with display mediums in a public place, such as cardboard standup displays, kiosks, and marquees.

Digital surveys present a unique challenge to survey administration because survey respondents are not only bombarded with digital content, but also insulated from survey administrators through a computing device and (oftentimes) a network. When a potential survey respondent responds to a digital survey using a mobile device or personal computer, for example, textual questions and responses often do not (or cannot) capture certain characteristics of a survey respondent, such as the survey respondent's age, attentiveness, or gender. Moreover, the insulation and anonymity of a computing device often prevents conventional digital survey systems from gathering information from a potential respondent to detect the respondent's interaction with (or unwritten reaction to) the digital survey. A survey respondent may, for example, misrepresent biographical information while taking a digital survey, watch a video while taking a digital survey, or perform another activity that distracts the respondent from the digital survey. Conventional digital survey systems may not detect such misrepresentation of information or distracted behavior.

Despite the value of knowing a survey respondent's activities, unwritten reactions, or other characteristics, conventional digital survey systems often cannot collect accurate data concerning certain characteristics of a survey respondent beyond asking the respondent to directly provide such information in response to textual questions. But survey respondents often provide unreliable information. Some conventional digital survey systems detect a limited scope of a survey respondent's characteristics by using a cookie to detect activity within a web browser or a software application to detect (or receives notifications of) functions performed by other software applications. But conventional digital survey systems fail to detect a survey respondent's reaction to specific survey questions, activity or attentiveness while taking a digital survey, or many other respondent characteristics. Conventional digital survey systems, therefore, lack effective mechanisms for capturing respondents' unwritten reactions to survey questions and certain other respondent characteristics.

Similar to digital surveys administered through personal computing devices, digital survey systems that use display mediums often cannot capture the engagement, activity, or other characteristics of a survey respondent. Survey administrators sometimes use big-screen televisions, shopping mall displays, billboards, or other display mediums to gather information concerning target populations. But like a computing device that displays digital content, certain public environments include numerous digital or physical display mediums that compete for the public's attention. Accordingly, shoppers, pedestrians, or other target audience members in a public place often lack the time or attention to take a survey on a kiosk or respond to an in-person survey. That lack of attention and time translates into a lack of data on a target population's impressions or reactions to a display medium.

Despite the value of detecting survey respondent's engagement, activities, or other characteristics, conventional display mediums often lack the ability to collect useful data concerning respondents who interact with (or disregard) a display medium. Although some conventional display mediums, for example, employ photoelectric infrared detectors to count passersby, such conventional display mediums do little more than detect the potential presence of a passerby, while failing to provide information or data concerning the person's engagement, activity, or other unwritten reactions.

Accordingly, these and other disadvantages decrease the utility of conventional digital survey systems and display mediums.

SUMMARY

This disclosure describes solutions to some or all the foregoing problems with systems and methods that administer a digital survey while collecting biometric data from a respondent of the digital survey. For instance, the systems and methods administer a digital survey to a respondent who interacts with a biometric sensor while participating in a digital survey. Moreover, the systems and methods analyze and convert biometric data into respondent characteristics. By converting biometric data into emotions, engagement levels, or other respondent characteristics, the disclosed systems and methods identify various unwritten or nonverbal responses of survey respondents who respond to a digital survey or who interact with a display medium that captures survey data. To facilitate review of respondents' characteristics and responses, in some embodiments, the disclosed systems and methods further categorize the converted respondent characteristics within a response database for the digital survey.

For instance, in some embodiments, the disclosed systems and methods receive biometric data captured by a biometric sensor as part of a digital survey. That biometric data may be captured, for example, in response to a biometric query from a digital survey question, in response to instructions sent to a display medium, or independently by a biometric sensor. In receiving the biometric data, the disclosed systems and methods likewise receive an identifier that triggers the systems and methods to analyze the biometric data for specific information— such as by analyzing an image to identify a physical characteristic or analyzing a data packet to identify a biometric measurement (e.g., heart rate). Based on the analysis, the disclosed systems and methods convert the biometric data to one or more respondent characteristics, such as an emotion, engagement level, or biographical detail of the respondent. The disclosed systems and methods then categorize the respondent characteristics within a response database for the digital survey.

By collecting and converting biometric data as part of administering a digital survey, the disclosed systems and methods identify respondent characteristics that conventional digital survey systems do not detect or that survey respondents often do not report. To identify such respondent characteristics, the biometric survey system collects biometric data that reflects the activities, unwritten reactions, or other characteristics of respondents engaging with digital survey questions or display mediums. Categorizing respondent characteristics into a response database further provides a more detailed and flexible dataset of digital survey responses that conventional digital survey systems often leave uncaptured. The response database further enables a digital survey system to more efficiently identify and parse respondents' responses according to respondent characteristics determined from the collected biometric data.

In addition to providing more specific data about survey respondents' unwritten reactions, the disclosed systems and methods further provide reports to administrator devices that arrange various respondent characteristics according to responses and interactions. For example, in some embodiments, the biometric survey system generates reports that indicate specific respondent characteristics that correspond to respondents' replies to textual queries. Such reports may, for example, identify a survey respondent's engagement level when reviewing a specific textual query. Alternatively, the biometric survey system may generate reports that identify biographical information or other respondent characteristics of those survey respondents most (or least) engaged with a display medium.

The following description sets forth additional features and advantages of one or more embodiments of the disclosed systems and methods. In some cases, such features and advantages will be obvious to a skilled artisan from the description or may be learned by the practice of the disclosed embodiments.

BRIEF DESCRIPTION OF THE DRAWINGS

The detailed description refers to the drawings briefly described below.

DETAILED DESCRIPTION

Figure 1:
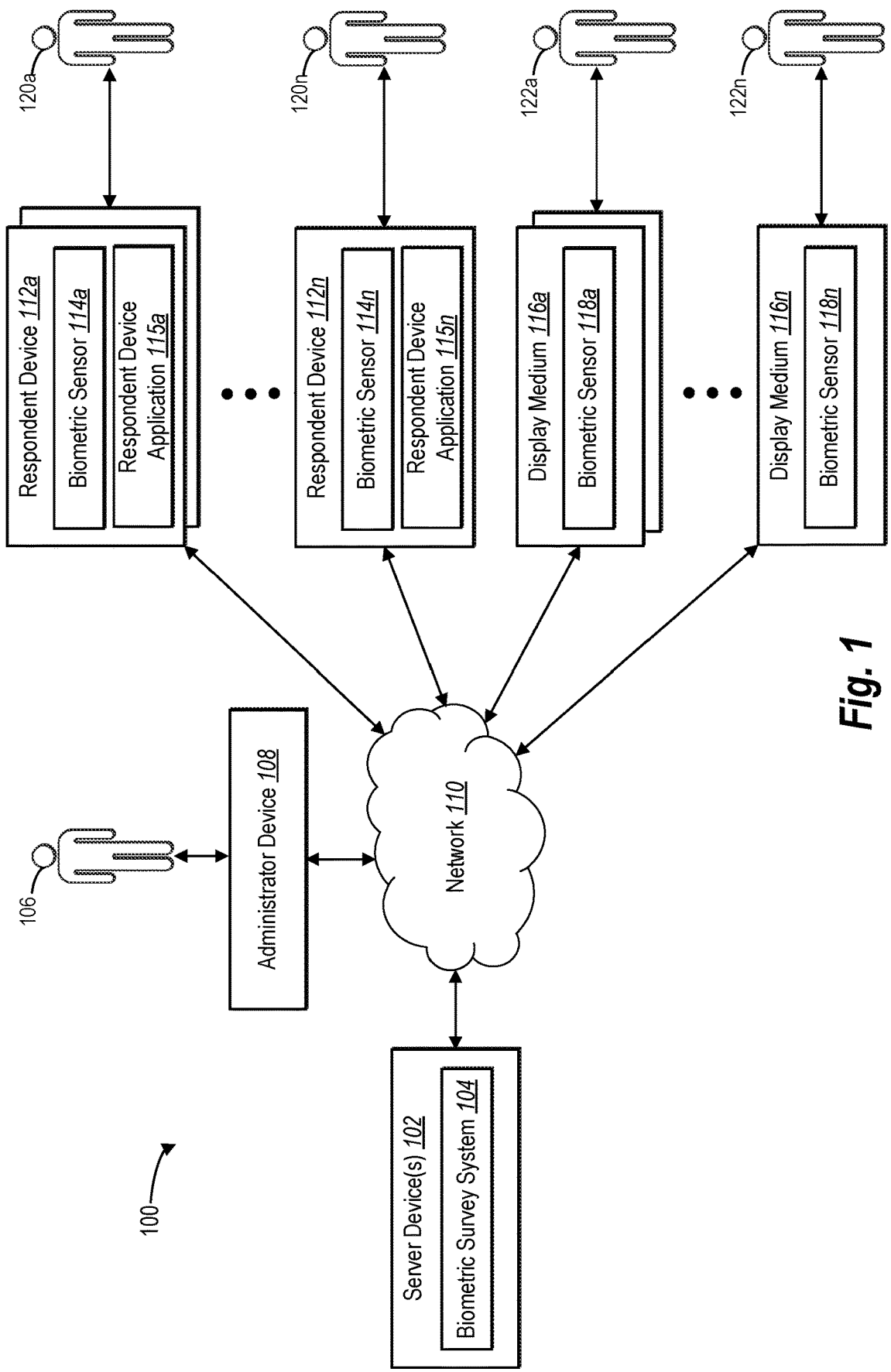
FIG. 1 illustrates a block diagram of an environment for implementing a biometric survey system in accordance with one or more embodiments.

This disclosure describes one or more embodiments of a biometric survey system that administers a digital survey to respondents who interact with a biometric sensor to collect and convert biometric data into respondent characteristics. By collecting biometric data, and subsequently converting the biometric data into emotions, engagement levels, or other respondent characteristics, the biometric survey system identifies various unwritten or nonverbal responses of survey respondents who respond to a digital survey or who interact with a display medium that captures survey data. To facilitate review of respondents' characteristics and responses, the biometric survey system categorizes the converted respondent characteristics within a response database for a digital survey.

For instance, in some embodiments, the biometric survey system provides a digital survey question to a client device as part of a digital survey. In some such instances, the digital survey question contains a textual query and a biometric query. The biometric survey system further receives a response to the digital survey question from a respondent using the client device. Accordingly, in some embodiments, the response to the digital survey question comprises a reply to the textual query and biometric data captured by a biometric sensor in response to the biometric query.

Based on receiving a response to the digital survey question, the biometric survey system then analyzes the biometric data within the response. For example, the biometric survey system may analyze biometric data in the form of an image (e.g., a digital photo) to identify a physical characteristic of the respondent. As another example, the biometric survey system may analyze a biometric measurement (e.g., heart rate) to determine an engagement level of the respondent. Based on that analysis, the biometric survey system converts the biometric data to a respondent characteristic (e.g., gender, emotion, or engagement level) and categorizes the respondent characteristic within a response database for the digital survey.

Similarly, in some embodiments, the biometric survey system receives biometric data from a biometric sensor associated with a display medium, such as a public advertisement display. In some such cases, the biometric data corresponds to a respondent who interacted with the display medium. In some embodiments, such biometric data is associated with a survey identifier that the survey system uses to determine how to process and analyze the biometric data. For example, based on the survey identifier or some other identifier, the biometric survey system may analyze a video to identify a physical characteristic of a respondent; an image to identify an accessory, child, pet, or other object associated with the respondent; or a data packet to identify a biometric measurement (e.g., breath rate, heart rate). Based on that analysis, the biometric survey system converts the biometric data to a respondent characteristic associated with a respondent and categorizes the respondent characteristic within a response database of the digital survey.

By receiving and converting biometric data as part of a digital survey, the disclosed biometric survey system automates the capture of respondent characteristics that conventional digital survey systems could not previously perform. Specifically, the biometric survey system identifies emotions, engagement levels, or other respondent characteristics that conventional digital survey systems do not detect or that survey respondents often do not report. To identify such respondent characteristics, the biometric survey system collects biometric data that reflects survey respondent's identities, activities, or unwritten reactions to digital survey questions or display mediums.

By further categorizing respondent characteristics into a response database, the biometric survey system provides a more detailed and flexible dataset of responses that conventional digital survey systems often leave uncaptured. The response database further enables a digital survey system to more efficiently (and precisely) identify respondents' responses and parse those responses by various characteristics detected by a biometric sensor. For example, in some embodiments, the biometric survey system organizes and sorts responses to digital surveys within a response database according to respondent emotion, engagement level, or biographical details. Both the conversion of biometric data and categorization of respondent characteristics improves the technology of digital survey systems by providing a dynamic snapshot of survey respondents that integrates responses with biometric measurements.

In addition to providing more specific data about survey respondents' unwritten reactions, the biometric survey system generates reports for administrator devices that arrange various respondent characteristics according to responses. For example, in some embodiments, the biometric survey system generates reports that indicate specific respondent characteristics that correspond to respondents' replies to textual queries. Such reports may, for example, identify a survey respondent's engagement level when reviewing a specific textual query. Alternatively, the biometric survey system may generate reports that identify biographical information or other respondent characteristics of those survey respondents most (or least) engaged with a display medium.

In addition to categorizing or reporting survey results according to respondent characteristics, in some embodiments, the biometric survey system targets potential respondents for a digital survey based on biometric data received from a biometric sensor. For example, after converting biometric data into respondent characteristics, the biometric survey system optionally targets respondents with characteristics filtered by a survey administrator (or by the digital survey system) to send a digital survey.

The biometric survey system not only targets potential respondents for a digital survey based on biometric data, but the system optionally tracks coupons issued as part of a digital survey. For example, in some embodiments, the biometric survey system generates coupons or receives notice that a coupon has been issued by a display medium using a coupon identifier. Based on the coupon identifiers, the biometric survey system may receive notices that a specific coupon has been redeemed as part of a transaction or determine that the coupon has expired without redemption. By tracking redemption of coupons by coupon identifier, the biometric survey system correlates transactions and coupon redemption with corresponding respondent characteristics within the response database.

Turning now to the figures, FIG. 1 provides an overview of an environment 100 in which a biometric survey system 104 can operate. After providing an overview of the environment 100, this disclosure describes embodiments of the biometric survey system 104 in more detail with reference to FIGS. 2-9.

As illustrated in FIG. 1, the environment 100 includes an administrator device 108 associated with a survey administrator 106. The environment 100 further includes respondent devices 112a through 112n (collectively referred to as "respondent devices 112") that are respectively associated with survey respondents 120a through 120n (collectively referred to as "survey respondents 120"). Each of the respondent devices 112a through 112n likewise respectively comprise a respondent device application 115a through a respondent device application 115n (collectively referred to as the "respondent device applications 115"). The survey respondents 120 may interact with the respondent device applications 115 to respond to digital survey questions. In some embodiments, the respondent device applications 115 comprise web browsers, applets, dedicated applications (e.g., dedicated digital survey applications), instant message applications, SMS applications, email applications, and/or other software applications available to the respondent devices 112.

The environment 100 also includes display mediums 116a through 116n (collectively referred to as "display mediums 116") that are associated with survey respondents 122a through 122n (collectively referred to as "survey respondents 122"). The survey respondents 122 interact with one or more of the display mediums 116. Although FIG. 1 illustrates one administrator device 108, a few respondent devices 112, and a few display mediums 116, the environment 100 may include any number of administrator devices associated with any number of survey administrators, any number of respondent devices associated with any number of survey respondents, or any number of display mediums associated with any number of survey respondents.

As further shown in FIG. 1, each of the respondent devices 112 and the display mediums 116 include a biometric sensor. The respondent devices 112a through 112n respectively include biometric sensors 114a through 114n (collectively referred to as "biometric sensors 114"). Additionally, the display mediums 116a through 116n respectively include biometric sensors 118a through 118n (collectively referred to as "biometric sensors 118").

As used in this disclosure, the term "display medium" refers to a physical means of exhibiting or projecting an image, product, sound, or text. For example, in some embodiments, a display medium includes a visual display of a physical image, product, or text. Such display mediums include, but are not limited to, a billboard, booth, cardboard-standup display, freestanding-graphic display, marquee, product display, or shopping-mall display that exhibit a product or show images. In some such embodiments, the display medium exhibits food or other physical objects that a survey respondent may smell, taste, touch, or view, such as a food-display stand or product-display booth. Conversely, in certain embodiments, a display medium includes a digital or electronic display or projection of audio, images, video, or text, such as a computer kiosk, television, or megatron display. For example, in some such embodiments, the display medium projects audio that a survey respondent can hear, such as a headphone display with headphones playing audio samples or a speaker stand with a speaker projecting music. Alternatively, the display medium may display a digital image or video on a screen, such a the megatron display.

The term "biometric sensor" refers to an instrument or device that captures biometric data representing a physical attribute of, or a physical measurement associated with, a person. Accordingly, the biometric sensors 114 and 118 (or any other biometric sensor) may comprise cameras, depth sensors, heart-rate monitors, microphones, touch sensors, or any other biometric sensor. Moreover, biometric sensors can capture biometric data either independent of capture instructions from the biometric survey system 104 or in response to capture instructions sent by the biometric survey system 104.

The term "biometric data" in turn refers to data that represents or depicts a physical attribute of, or a physical measurement associated with, a person. Biometric data may include, for example, an audio recording (e.g., voice recording), a blood-pressure measurement, a blood-sugar measurement, a breath rate, a heart rate, an image, or a video captured by a biometric sensor. In one or more embodiments, the biometric data is associated with a user participating in a digital survey, or with a user interacting with a display medium. In additional embodiments, the biometric data is associated with an exercise-workout session, such as a breath rate or heart rate associated with an aerobic, elliptical, gym, running, swimming, treadmill, weight-lifting, yoga, or any other type of exercise-workout session. In other embodiments, the biometric data is associated with a medical appointment, medical check-up, insurance examination, or routine biometric collection, such as a blood-pressure, blood-sugar, breath-rate, or heart-rate measurement associated with a doctor's appointment or a routine sample.

In general, the administrator device 108, the respondent devices 112, and the display mediums 116 communicate with server device(s) 102, including the biometric survey system 104, over a network 110. As described below, the server device(s) 102 enable various functions, features, processes, methods, and systems described herein using, for example, the biometric survey system 104. Additionally, or alternatively, the server device(s) 102 coordinate with the administrator device 108, the respondent devices 112, and/or the display mediums 116 to perform or provide the various functions, features, processes, methods, and systems described in more detail below. Although FIG. 1 illustrates a particular arrangement of the server device(s) 102, the administrator device 108, the respondent devices 112, the display mediums 116, and the network 110, additional arrangements are possible. For example, the server device(s) 102 and the biometric survey system 104 may directly communicate with the administrator device 108 and thus bypass the network 110.

Within the arrangement shown in FIG. 1, the administrator device 108, the respondent devices 112, and the display mediums 116 can include any one of various types of client devices. For example, the administrator device 108, the respondent devices 112, and the display mediums 116 can be mobile devices, tablets, laptop computers, desktop computers, smart televisions, televisions, monitors, or any other type of computing device, as further explained below with reference to FIG. 10. In some embodiments, however, the display mediums 116 are associated with a computing device. Such display mediums 116 may comprise any display medium consistent with the examples above, including, but not limited to, billboards, cardboard-standup displays, computer kiosks, freestanding-graphic displays, marquees, shopping-mall displays, or televisions. In such embodiments, the display mediums 116 are associated with a computing device.

Additionally, the server device(s) 102 can include one or more computing devices, including those explained below with reference to FIG. 10. The administrator device 108, the respondent devices 112, the display mediums 116, server device(s) 102, and network 110 may communicate using any communication platforms and technologies suitable for transporting data and/or communication signals, including any known communication technologies, devices, media, and protocols supportive of data communications, examples of which are described with reference to FIG. 11.

As an overview of the environment 100, the server device(s) 102 provide the administrator device 108 access to the biometric survey system 104 through the network 110. In one or more embodiments, by accessing the biometric survey system 104, the server device(s) 102 provide one or more digital documents (e.g., webpages) to the administrator device 108 to allow the survey administrator 106 to compose a digital survey. The digital documents include tools and options that facilitate composing a digital survey for distribution to the respondent devices 112 or the display mediums 116.

As used in this disclosure, the term "digital survey" refers to a digital communication that collects information concerning one or more respondents by capturing information from (or posing questions to) such respondents. Accordingly, a digital survey may include one or more digital survey questions. Alternately, a digital survey may capture responses without digital survey questions, such as by capturing biometric data from respondents who interact with a display medium.

The term "digital survey question" in turn refers to a prompt within a digital communication that invokes a response from a respondent. A digital survey question may include a textual query and/or a biometric query. The term "textual query" refers to human-readable characters that form a question. For example, a textual query includes interrogative sentences (e.g., "How are you?") and imperative sentences (e.g., "Please identify the clothing brand you prefer") written in text. Textual queries may come in various formats, including but not limited to, multiple choice, open-ended, ranking, scoring, summation, demographic, dichotomous, differential, cumulative, dropdown, matrix, net promoter score ("NPS"), single textbox, heat map, or any other type of formatting prompt that invokes a response from a respondent.

By contrast, the term "biometric query" refers to a directive to collect biometric data. For example, a biometric query includes a directive to a biometric sensor to capture images or data representing physical attributes (e.g., heart rate, facial features). In some embodiments, a biometric query may be associated with a textual query. In such cases, for example, the biometric query may comprise computer-executable instructions to a biometric sensor to capture certain biometric data while a client device presents a textual query. The computer-executable instructions may comprise instructions to the respondent device 112*a* to cause a camera to record the survey respondent 120*a* while the respondent device 112*a* presents a textual query.

Referring back now to FIG. 1, in certain embodiments, the biometric survey system 104 provides tools to the administrator device 108 for the survey administrator 106 to compose one or more digital survey questions that comprise a textual query and/or a biometric query for distribution to the respondent devices 112. Additionally, in some embodiments, the biometric survey system 104 provides selectable options for a digital survey question to include a textual query without a biometric query, a biometric query without a textual query, or a textual query and a biometric query together.

In addition to tools to compose digital survey questions, in certain embodiments, the biometric survey system 104 provides tools for the survey administrator 106 to compose a digital survey for a display medium. In some such embodiments, the digital survey comprises a survey identifier that uniquely identifies a digital survey, as well as one or more associated response classifiers. The term "response classifier" refers to a code, identifier, or other data object that indicates the type of biometric data collected by a digital survey. For example, a response classifier may include a code that indicates that certain data comprises an audio recording, breath rate, heart rate, image, video, or some other biometric data. A response classifier may further indicate data associated with biometric data, such as depth measurements that indicate a distance between a survey respondent and a biometric sensor.

As detailed further below, in some embodiments, the response classifier further includes capture instructions for a display medium (or a computing device associated with a display medium) to cause a biometric sensor to capture specific biometric data (e.g., an image, video, heart rate, scan). Moreover, in some embodiments, a survey identifier optionally includes a response classifier or indicates any information indicated by a response classifier. While this disclosure primarily describes a response classifier as separate from a survey identifier, certain embodiments of the biometric survey system 104 may use a survey identifier that includes a response classifier or identifies the same information as a response classifier when sending or receiving data from the display mediums 116.

After the survey administrator 106 composes a digital survey, the biometric survey system 104 causes the server device(s) 102 to send the digital survey to one or more of the respondent devices 112, such as the respondent device 112a, or one or more of the display mediums 116, such as the display medium 116a. For example, the biometric survey system 104 can provide a digital survey comprising multiple digital survey questions (each of which comprise a textual query and at least one biometric query) to the respondent device 112a. Alternatively, the biometric survey system 104 can provide a digital survey comprising a survey identifier and one or more response classifiers to the display medium 116a.

Upon receiving a digital survey, the respondent device 112a, for example, presents the textual queries of the digital survey to the survey respondent 120a. The survey respondent 120a may respond to textual queries within the digital survey by providing user input via the respondent device application 115a (e.g., by selecting an answer using a touch screen or a mouse, or by inputting text data using a keyboard). The survey respondent 120a likewise responds to any biometric queries, but in a different way. The biometric sensor 114a captures biometric data concerning the survey respondent 120a in response to any biometric queries within the digital survey, such as by capturing an audio recording, breath rate, heart rate, image, or video.

After the survey respondent 120a replies to a textual query (within a digital survey) using the respondent device application 115a—and the biometric sensor 114a captures corresponding biometric data—the respondent device application 115a instructs the respondent device 112a to send a data packet representing a response to the server device(s) 102. Upon receipt of the data packet, the biometric survey system 104 directs the storage and analysis of the data packet, including the biometric data. Moreover, in some embodiments, the biometric survey system 104 converts the biometric data into one or more respondent characteristics.

As used in this disclosure, the term "respondent characteristic" refers to a trait or feature exhibited or embodied by a survey respondent based on biometric data. For instance, the digital survey system determines a respondent characteristic (e.g., an emotion) based on analyzing an image of the user (e.g., by detecting the respondent is smiling in the image). Accordingly, a respondent characteristic includes behavioral traits that a survey respondent exhibits, such as the behaviors of engaging with a digital survey question or display medium through eye contact or expressing an emotion while responding to a digital survey question or interacting with a display medium. In some embodiments, a respondent characteristic includes information associated with exercise-workout sessions, medical appointments, or routine biometric collections, such as a number of exercise-workout sessions that a survey respondent performs within a week, month, or year (e.g., number of runs or yoga sessions), a number of medical appointments for a survey respondent within a week, month, or year, or a name of a pharmaceutical or medical device used by a survey respondent. A respondent characteristic also includes physical traits of a survey respondent, including, but not limited to, an age, eye color, hair color, height, gender, race, or weight.

Similar to the respondent device 112a, upon receiving a digital survey, the display medium 116a, for example, uses the biometric sensor 118a to capture biometric data. The biometric sensor 118a may have different triggers for capturing biometric data. In some embodiments, the biometric sensor 118a captures biometric data based on predetermined instructions within the biometric sensor 118a—independent of instructions received from the digital survey. Alternatively, in other embodiments, the biometric sensor 118a captures biometric data in response to instructions sent from the biometric survey system 104, such as instructions within a response classifier. When capturing the biometric data, the biometric sensor 118a may capture audio recordings, breath rates, heart rates, images, videos, or any other biometric data indicated by a response classifier.

After the biometric sensor 118a captures the biometric data, and regardless of the trigger for capturing the biometric data, the display medium 116a sends the biometric data to the server device(s) 102. When sending the biometric data, the display medium 116a may send, for example, a data packet that includes the biometric data, survey identifier, and response classifier, among other things. Upon receipt of the data packet, the biometric survey system 104 directs the storage and analysis of the biometric data. In some embodiments, the biometric survey system 104 converts the biometric data into one or more respondent characteristics.

Figure 2A:
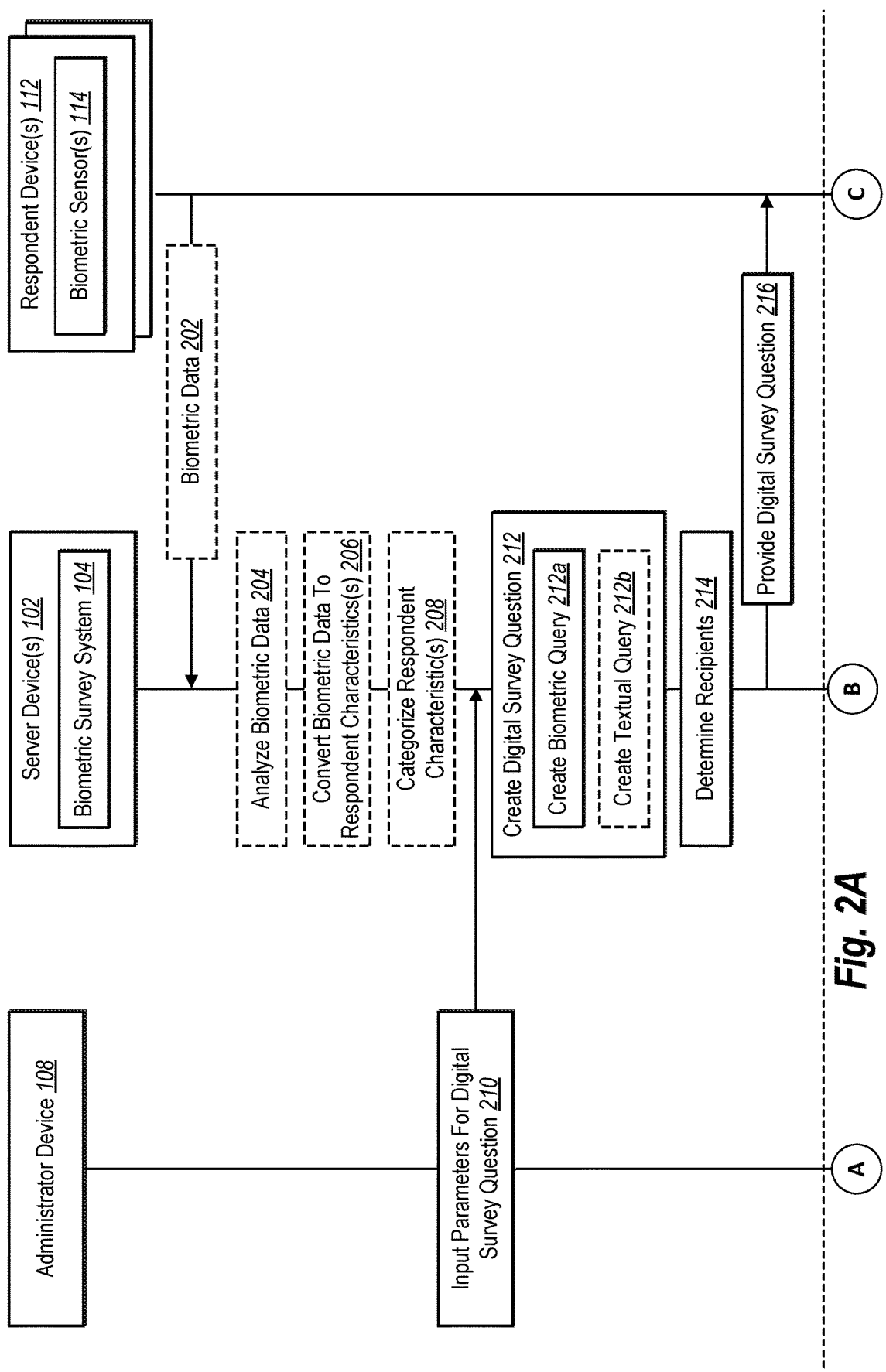
FIGS. 2A-2B illustrate a sequence-flow diagram of converting biometric data into respondent characteristics associated with respondent replies to textual queries in accordance with one or more embodiments.
Figure 2B:
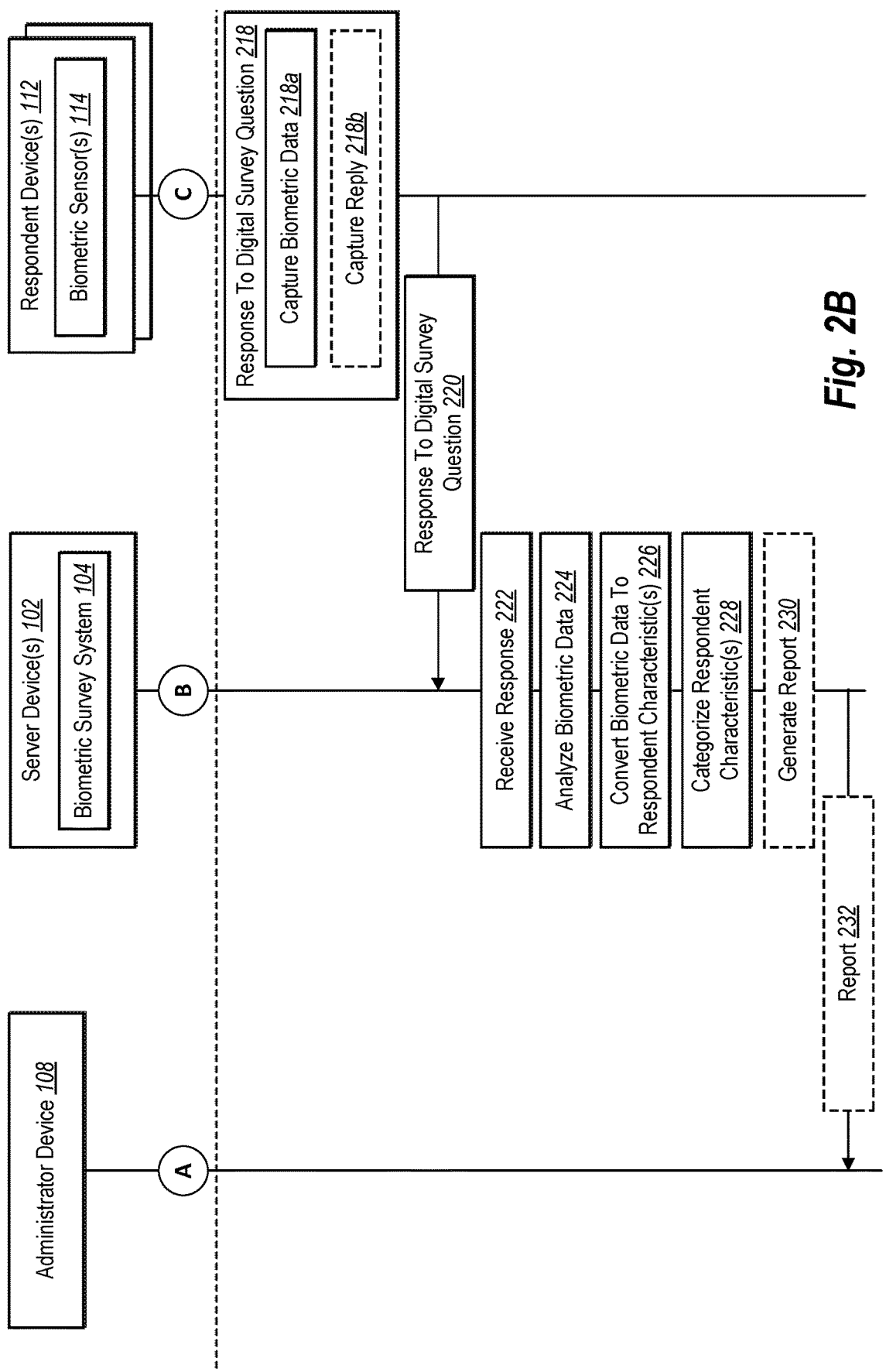

Turning now to FIGS. 2A-2B, these figures provide an overview of embodiments of the biometric survey system 104 that administer digital surveys to respondents to collect and convert biometric data into respondent characteristics for categorization within a response database. Specifically, FIGS. 2A-2B illustrate a representation of a sequence of acts 202-232 that the server device(s) 102, the administrator device 108, or the respondent devices 112 perform to, among other things, collect and convert biometric data into respondent characteristics for categorization within a response database. For instance, in some embodiments, the server device(s) 102, administrator device 108, or respondent devices 112 include computer-executable instructions that, when executed by a processor thereon, cause the server device(s) 102, administrator device 108, or respondent devices 112 to perform one or more of the acts 202-232 shown in FIGS. 2A-2B.

For ease of reference, the following paragraphs describe the biometric survey system 104 as performing one or more of the acts 202-232 rather than the server device(s) 102. As suggested above, the biometric survey system 104 comprises computer-executable instructions that cause the server device(s) 102 to perform one or more of the acts 202-232. Rather than repeatedly describe the relationship between the instructions within the biometric survey system 104, on the one hand, and the server device(s) 102, on the other hand, this disclosure will describe the biometric survey system 104 as performing the acts as a shorthand for that relationship. Additionally, while the paragraphs below often describe the acts 202-232 in relation to a single digital survey question and a single response to the digital survey question, certain embodiments of the acts 202-232 involve multiple digital survey questions and multiple responses to the digital survey questions.

Turning back now to the acts 202-232, as noted above, the biometric survey system 104 optionally targets potential respondents for a digital survey based on biometric data received from biometric sensors. As part of this targeting process, and as shown in FIG. 2A, the biometric survey system 104 optionally performs act 202 of receiving biometric data transmitted by the respondent devices 112. After receipt of the biometric data, the biometric survey system 104 optionally performs act 204 of analyzing the biometric data and, thereafter, optionally performs act 206 of converting the biometric data to respondent characteristic(s). The following paragraphs describe each of the acts 202, 204, and 206 in turn.

When performing act 202, the biometric survey system 104 receives (and the respondent devices 112 transmit) various identifiers with the biometric data to facilitate the processing of the biometric data. For example, in some embodiments, the respondent devices 112 transmit the biometric data within a data packet to the biometric survey system 104. Such a data packet may include an associated respondent identifier and an associated question identifier or response classifier. As used in this disclosure, the term "question identifier" refers to a code, indicator, metadata, or other data object associated with a digital survey question. A question identifier likewise identifies one or more biometric data analyses for a given digital survey question. For example, a question identifier may identify a face recognition algorithm or heart-rate analysis for the biometric survey system 104 to perform on biometric data associated with the question identifier.

As explained further below, in some embodiments, the respondent devices 112 transmit a data packet comprising biometric data and a question identifier when the survey respondents 120 respond to a digital survey question. Alternatively, in other embodiments, the respondent devices 112 transmit a data packet comprising biometric data and a response classifier independent of (and without a response to) a digital survey question.

Independent of the components of a data packet, in some embodiments, the respondent devices 112 send (and the biometric survey system 104 receives) a data packet comprising a response classifier and biometric data gathered for other software applications. In some such embodiments, the data packet comprises a response classifier without a question identifier because the respondent devices 112 transmit the data packet independent of a digital survey question. For example, after receiving a grant of permission from the survey respondent 120a to access biometric data, the respondent device application 115a optionally accesses biometric data stored on the respondent device 112a (or on a computing device synchronized with the respondent device 112a). This biometric data may have been captured by biometric sensors for the respondent device application 115a or for an additional software application. To illustrate, such biometric data may include breath-rate or hear-rate measurements associated with an exercise-workout session tracked by a software application or, alternatively, a medical check-up or appointment tracked by a software application. The additional software application may include, but is not limited to, a running, gym, or other exercise software application or a medical or insurance software application on a mobile device.

Additionally, as part of transmitting the data packet for act 202, the respondent devices 112 optionally transmit additional information associated with exercise-workout sessions, medical appointments, or routine biometric collections with a grant of permission from the survey respondent. For example, the respondent devices 112 may transmit a number of exercise-workout sessions or medical appointments per week, month, or other time period or, alternatively, a name of a pharmaceutical or medical device prescribed in connection with a medical appointment or routine biometric collection. In some such embodiments, the data packet comprises the additional information. Based on the granted permission, the respondent device 112a sends the biometric data (and any additional associated information) to the biometric survey system 104.

Referring back now to FIG. 2A, regardless of whether the respondent devices 112 transmit question identifiers or response classifiers with biometric data, question identifiers and response classifiers both serve as triggers for the biometric survey system 104 to select a biometric data analysis to apply to the received biometric data. As noted above, after receiving biometric data, the biometric survey system 104 optionally performs act 204 of analyzing the biometric data. When performing act 204, the biometric survey system 104 selects a biometric data analysis based on a question identifier or response classifier received within a data packet. In such cases, the question identifier or response classifier indicates one or more biometric data analyses for the biometric survey system 104 to apply to the biometric data.

For example, in some embodiments, a question identifier or response classifier comprises an alphanumeric code, metadata, binary code, or some other indicator that corresponds to a face recognition algorithm that determines gender. When performing act 204, the biometric survey system 104 selects and applies the face recognition algorithm to the image captured by the biometric sensor 114a based on the question identifier. By applying the face recognition algorithm, the biometric survey system 104 measures certain features of the face and head of the survey respondent 120a captured within the image.

The foregoing question identifier provides one example of the relationship between a question identifier (or a response classifier) and a biometric data analysis. In additional embodiments, when performing the acts 202 and 204, the biometric survey system 104 may receive a question identifier or response classifier that triggers the biometric survey system 104 to apply one or more of the following biometric data analyses to the received biometric data: (i) an audio analysis to identify a digital file representing audio of a survey respondent; (ii) a blood-pressure analysis to identify systolic and diastolic blood-pressure measurements in millimeters of mercury ("mmHg") within the received biometric data; (iii) a breath-rate analysis to identify a respiratory measurement in breaths per minute within the received biometric data; (iv) facial recognition algorithms to identify accessories, eye features, facial features, or hair features of a face or head within an image or video from within the received biometric data; and (v) a heart-rate analysis to identify a heart-rate measurement in beats per minute within the received biometric data.

As just referenced, when performing act 204 shown in FIG. 2A, the biometric survey system 104 optionally applies facial recognition algorithms to analyze captured images or videos. In certain instances, the biometric survey system 104 applies facial recognition algorithms to detect and measure the distance among facial features shown in an image (or multiple images from a video), including, for example, a hairline, forehead, left eyebrow, right eyebrow, *glabella*, left eye, right eye, nose bridge, nose tip, left nostril, right nostril, scar, mole, freckle, pimple, left ear, right ear, lip curve, tubercle of an upper lip, top portion of a lip, bottom portion of a lip, mouth corner, or chin. Additionally, in some embodiments, the biometric survey system 104 applies facial recognition algorithms to detect and measure colors of facial or head features, including, for example, eye color, hair color, or skin tone, and/or to detect and measure the presence and dimensions of certain facial features, including, for example, facial hair, cranial hair, or laryngeal prominences (a.k.a. Adam's apples). Moreover, in some embodiments, the biometric survey system 104 applies facial recognition algorithms to detect and measure accessories, including, for example, ear rings, glasses, hats, headdress, jewelry, lip rings, make-up, nose rings, or scarves.

When applying a facial recognition algorithm as part of act 204, in some cases, the biometric survey system 104 applies well-known techniques or more recently developed facial recognition algorithms. For example, the biometric survey system 104 optionally applies Elastic Bunch Graph Matching, a hidden Markov model, an Eigenface algorithm, a Face++ algorithm, Fisherface algorithm, a GaussianFace algorithm, a Human Perception Based Fusion Scheme ("HPFS"), multilinear subspace learning, or neuronal motivated dynamic link matching. GaussianFace is described by Chaochao Lu and Xiaoou Tang, "Surpassing Human-Level Face Verification Performance on LFW with GaussianFace," Proceedings of the 29th AAAI Conference on Artificial Intelligence (AAAI-15) (2014), which is incorporated in its entirety by reference. HPFS is described by Daksha Yadav, Richa Singh, Mayank Vatsa, and Afzel Noore, "Recognizing Age-Separated Face Images: Humans and Machines," PLOS ONE (December 2014), which is likewise incorporated in its entirety by reference. In some embodiments, the biometric survey system 104 uses a facial Application Program Interface ("API"), such as Microsoft Corporation's Face API, to apply a facial recognition algorithm.

When applying various facial recognition algorithms as part of act 204, in some embodiments, the biometric survey system 104 detects and measures any of the foregoing accessories, eye features, facial features, or hair features. As explained below, such detection and measurements form a basis for the biometric survey system 104 to perform an embodiment of act 206 by converting biometric data into a biographic classification for a respondent, such as an age classification, gender classification, or a race classification. To facilitate such biographic classifications, in some embodiments, the biometric survey system 104 detects and measures some or all of the foregoing accessories, eye features, facial features, or hair features as part of a facial recognition algorithm that determines age, gender, or race.

In addition to different versions of facial recognition algorithms, when performing act 204, the biometric survey system 104 may apply a facial recognition algorithm as part of a broader biometric data analyses. Such biometric data analyses correspond to a specific conversion of biometric data into a respondent characteristic for act 206. For example, in some embodiments, a question identifier or response classifier triggers the biometric survey system 104 to apply an emotion analysis that includes one or more of the blood-pressure analysis, breath-rate analysis, heart-rate analysis, voice-print analysis, and a facial recognition algorithm. In such embodiments, the biometric survey system 104 applies the facial recognition algorithm to detect and measure facial features in an image or video that form facial expressions. For example, the biometric survey system 104 optionally uses an Emotion Application Program Interface ("API"), such as Microsoft Corporation's Emotion API, to determine an emotion exhibited by a survey respondent.

Additionally, in some embodiments, a question identifier or response classifier triggers the biometric survey system 104 to apply an engagement-level analysis that includes one or more of the blood-pressure analysis, breath-rate analysis, heart-rate analysis, and a facial recognition algorithm that detects eye movements within a video or multiple images. For example, in some embodiments, the biometric survey system 104 uses the Labeled Faces in the Wild ("LFW") library or Open Source Computer Vision Library ("OpenCV") combined with any of the facial recognition techniques described above to analyze and recognize the eye movements of a survey respondent.

As further shown in FIG. 2A, in addition to performing act 204 of analyzing the biometric data, the biometric survey system 104 optionally performs act 206 of converting the biometric data to respondent characteristic(s). In some cases, the biometric survey system 104 converts one or more outputs of a biometric data analysis (or a combination of biometric data analyses) into a respondent characteristic of a survey respondent. By contrast, the biometric survey system 104 optionally converts the biometric data into one or more respondent characteristics as part of the biometric data analysis. For example, the biometric survey system 104 may convert biometric data to a respondent characteristic when applying a facial recognition algorithm to identify a biographic classification for a survey respondent.

When performing act 206 shown in FIG. 2A, in some embodiments, the biometric survey system 104 converts biometric data into a respondent emotion. In converting biometric data into a respondent emotion, the biometric survey system 104 converts the output of an emotion analysis into a respondent emotion. In certain embodiments, for instance, the biometric survey system 104 combines a weighted score for one or more of an audio recording, blood pressure, breath rate, or heart rate with a weighted score for facial features detected by a facial recognition algorithm. Based on the average, sum, or product of the weighted scores, the biometric survey system 104 determines that the survey respondent 120a expresses a positive emotion, a neutral emotion, or a negative emotion. Alternatively, in some embodiments, the biometric survey system 104 determines that the survey respondent 120a expresses a strong emotion, a moderate emotion, or a weak emotion based on the average, sum, or product of the weighted scores.

For example, in some embodiments, the biometric survey system 104 assigns a score to one or more of facial features, audio recordings, blood pressure, breath rate, and heart rate of the survey respondent 120a as a precursor to converting the biometric data to an emotion. To illustrate, in some embodiments, the biometric survey system 104 assigns unique scores to facial features detected by a facial recognition algorithm, such as a unique score for facial features categorized according to the Facial Action Coding System ("FACS"). In such embodiments, the unique scores correspond to the following emotion categories: anger, contempt, fear, disgust, happiness, neutral, sadness, or surprise.

Similarly, in certain embodiments, the biometric survey system 104 assigns a score to an audio recording while the respondent device 112a presents a textual query. To assign the score, the biometric survey system 104 compares a voice's pace, pitch, resonance, timber, and/or tone within the captured audio recording to the same voice features within a previously recorded voice sample of the survey respondent 120a. By using a voiceprint analysis to compare the two voice samples, the biometric survey system 104 assigns a score to the captured audio recording.

Additionally, in some embodiments, the biometric survey system 104 assigns a score to a blood pressure, breath rate, and/or heart rate captured while the respondent device 112a presents a textual query to the survey respondent 120a. To assign the score, the biometric survey system 104 compares the captured blood pressure, breath rate, and/or hear rate to a previously captured blood pressure, breath rate, and/or heart rate of the survey respondent 120a.

The biometric survey system 104 then uses the scores described above to convert the biometric data to an emotion exhibited by the survey respondent 120a. For example, based on a weighted average, sum, or product of the score for the facial features, audio recording, blood pressure, breath rate, and/or heart rate, the biometric survey system 104 determines that the survey respondent 120a expresses a positive emotion, a neutral emotion, or a negative emotion.

In addition to converting biometric data into a respondent emotion, the biometric survey system 104 optionally associates a respondent emotion with a reply to a textual query. In some embodiments, for example, the biometric survey system 104 converts the biometric data into a respondent emotion associated with a reply to a textual query. Specifically, when performing act 206 to convert biometric data into a respondent emotion, the biometric survey system 104 optionally determines that the survey respondent 120a expresses a positive emotion, a neutral emotion, or a negative emotion—or a more specific emotion (e.g., happy, sad, frustrated)—while the respondent device 112a presents a textual query. That presentation may be during the entire presentation of the textual query or during the input of a reply by the survey respondent 120a only.

Additionally, in some embodiments, the biometric survey system 104 converts biometric data into emotion categories more specific than a positive, neutral, or negative emotion— including, but not limited to, the emotion categories of anger, contempt, fear, disgust, happiness, neutral, sadness, and surprise. For example, the biometric survey system 104 optionally determines that the survey respondent 120a expresses one of the prior emotion categories by using computer vision techniques to perform facial emotion recognition or by using an Emotion API.

Building on the unique scores described above, in some embodiments, the biometric survey system 104 adjusts a unique score for facial features under FACS that correspond to anger, contempt, fear, disgust, happiness, neutral, sadness, or surprise based on the one or more scores for an audio recording, blood pressure, breath rate, and/or heart rate. Based on the adjusted score, the biometric survey system 104 either confirms that the one or more scores support a determination that the survey respondent 120a expresses anger, contempt, fear, disgust, happiness, neutral, sadness, or surprise, or changes the determination to a different emotion category.

In addition to converting biometric data into a respondent emotion, in some embodiments, when performing act 206, the biometric survey system 104 converts biometric data into a respondent-engagement level. When converting biometric data into a respondent-engagement level, the biometric survey system 104 converts the output of an engagement-level analysis into a respondent-engagement level of a survey respondent.

For example, in certain embodiments, the biometric survey system 104 combines a weighted score for one or more of a blood pressure, breath rate, or heart rate with a weighted score for eye-movement patterns detected by a facial recognition algorithm. Based on the average, sum, or product of the weighted scores, the biometric survey system 104 determines that the survey respondent 120a shows a certain respondent-engagement level. In some such embodiments, the respondent-engagement levels fall within a scale of one to ten, with one representing the lowest engagement and ten representing the highest engagement. The biometric survey system 104, however, may use any appropriate scale or scoring system to identify respondent-engagement levels (e.g., by using engagement categories, including, highly engaged, moderately engaged, moderately unengaged, highly unengaged).

In some embodiments, when scoring eye movement detected by a facial recognition algorithm, the biometric survey system 104 uses a hidden Markov model based approach to analyze eye movement data from the survey respondent 120a. Based on a detected eye-movement pattern, the biometric survey system 104 assigns a score to the detected eye movement that represents a respondent-engagement level (e.g., a score of ten representing the highest engagement and a score of one representing the lowest engagement).

Additionally, the biometric survey system 104 optionally assigns a score to a blood pressure, breath rate, and/or heart rate captured while the respondent device 112a presents a textual query. To assign the score, the biometric survey system 104 compares the captured blood pressure, breath rate, and/or heart rate to a previously captured blood pressure, breath rate, and/or heart rate of the survey respondent 120a. Based on a weighted average, sum, or product of the score for the eye movement, blood pressure, breath rate, and/or heart rate, the biometric survey system 104 determines that the survey respondent 120a demonstrates a respondent-engagement level.

As suggested above, in some embodiments, the biometric survey system 104 converts biometric data into a respondent-engagement level associated with a reply to a textual query. Specifically, when performing act 206, the biometric survey system 104 optionally determines that the survey respondent 120a demonstrates a certain respondent-engagement level while the respondent device 112a presents a textual query. As noted above, that presentation may be during the entire presentation of the textual query or during the input of a reply by the survey respondent 120a only.

In addition to converting biometric data to a respondent-engagement level, in some embodiments, when performing act 206, the biometric survey system 104 converts biometric data into one or more biographic classifications for a survey respondent. In such embodiments, the biometric survey system 104 applies a facial recognition algorithm to convert the biometric data into one or more biographic classifications. Consistent with the disclosure above, the biometric survey system 104 applies a facial recognition algorithm to an image or video to determine a respondent's age (e.g., from 1 year old to 100 years old), a facial recognition algorithm to an image or video to determine a respondent's gender (e.g., male or female), or a facial recognition algorithm to an image or video to determine a respondent's race. As for the latter, the biometric survey system 104 determines a respondent's race using race categories from the U.S. Office of Management and Budget, including, Asian, black, white, native American, or Native Hawaiian and Pacific Islander.

As further shown in FIG. 2A, in addition to analyzing and converting biometric data into respondent characteristics, the biometric survey system 104 optionally performs act 208 of categorizing respondent characteristic(s). In particular, act 208 includes categorizing respondent characteristics within a response database for a digital survey. Alternatively, act 208 includes categorizing respondent characteristics within a response database that integrates information from multiple digital surveys. Additionally, in some embodiments, act 208 includes categorizing additional information received from the respondent devices 112 associated with exercise-workout sessions, medical appointments, or routine biometric collections.

As used in this disclosure, the term "response database" refers to a database within which the biometric survey system 104 stores responses (or data converted from the responses) to one or more digital surveys, including respondent characteristics. For example, the biometric survey system 104 may categorize and store respondent identifiers, survey respondents' replies to textual queries, and associated respondent characteristics converted from biometric data, among other things, within a response database. As another example, the biometric survey system 104 may categorize and store survey identifiers, respondent identifiers, and associated respondent characteristics converted from biometric data, among other things, within a response database. A response database may comprise any number of categories for responses to a digital survey or information associated with such responses, including, but not limited to, a coupon identifier (see FIG. 6C below), geographic location of the respondent, question identifier, respondent identifier, reply to a textual query, survey identifier, and a respondent characteristic. This disclosure describes additional embodiments of response databases with reference to FIGS. 3B and 6C below.

When performing act 208, the biometric survey system 104 optionally categorizes and sorts responses to digital surveys and/or respondent characteristics of survey respondents according to various categories. For example, in some embodiments, the biometric survey system 104 categorizes respondent characteristics within a response database of a digital survey according to a survey identifier, question identifier, respondent identifier, and/or any other information associated with a response to a digital survey. The biometric survey system 104 likewise (and optionally) sorts a response database by response or any information associated with a response to a digital survey (e.g., by response identifier, respondent characteristic). In other words, the response database is sortable by any of its constituent categories.

By categorizing and sorting a response database, the biometric survey system 104 enables the survey administrator 106 to target potential survey respondents having certain respondent characteristics. As explained further below, by categorizing and sorting a response database, the biometric survey system 104 facilitates targeting specific recipients to send a digital survey.

Independent of whether the biometric survey system 104 categorizes response characteristics as part of act 208, the administrator device 108 performs act 210 of receiving and sending input parameters for a digital survey question. As noted above, the biometric survey system 104 provides tools to the administrator device 108 for the survey administrator 106 to compose one or more digital survey questions. To facilitate the composition of such digital survey questions, the biometric survey system 104 provides tools, selectable options, and/or menus within a graphical user interface to compose a textual query and/or a biometric query.

For example, in some embodiments, the biometric survey system 104 provides a digital survey template to the administrator device 108 for presentation within a graphical user interface. In such embodiments, the digital survey template comprises a digital space in which the survey administrator 106 may compose, format, edit, and/or otherwise create one or more digital survey questions. In particular, in some embodiments, the biometric survey system 104 provides digital survey templates (or "electronic survey templates") as described in application Ser. No. 15/339,169, filed Oct. 31, 2016, entitled Guiding Creation of an Electronic Survey, which is hereby incorporated by reference in its entirety.

To facilitate biometric queries, in some embodiments, the biometric survey system 104 provides to the administrator device 108 selectable options (for presentation within the graphical user interface) to add a biometric query. For example, some selectable options—when selected—cause the biometric survey system 104 to add a biometric query by itself to a digital survey. Alternatively, some other selectable options—when selected—cause the biometric survey system 104 to add and associate a biometric query to a textual query. Regardless of how the selectable option is presented, in some embodiments, the biometric survey system 104 provides selectable options to add a biometric query comprising computer-executable instructions for a biometric sensor to capture an audio recording, breath rate, heart rate, image, video, or any other biometric data.

After receiving input parameters for a digital survey question, and as part of act 210, the administrator device 108 sends (and the biometric survey system 104 receives) the input parameters that form the basis for the digital survey question. Based on the received input parameters, the biometric survey system 104 performs act 212 of creating a digital survey question. Depending on the input parameters, the biometric survey system 104 performs act 212a of creating a biometric query and optionally performs act 212b of creating a textual query. For example, in some embodiments, the biometric survey system 104 generates a digital survey data packet that includes one or more data objects corresponding to one or more digital survey questions. These digital survey questions each in turn comprise one or more biometric queries and/or a textual query.

In addition to creating one or more digital survey questions, the biometric survey system 104 performs act 214 of determining recipients to whom a digital survey is sent. In certain embodiments, the biometric survey system 104 determines recipients of a digital survey based on a list of addresses or locators (e.g., email addresses, IP addresses, phone numbers, handles) received from the administrator device 108. Alternatively, in certain embodiments, the biometric survey system 104 determines recipients of a digital survey using a response database.

When using a response database to perform act 214, the biometric survey system 104 optionally suggests potential recipients for a digital survey based on certain respondent characteristics within a response database. As noted above, in certain embodiments, the response database integrates information from multiple digital surveys. Additionally, in some embodiments, the response database integrates information from multiple surveys and any other source from which biometric data is collected (e.g., biometric data collected from software applications on respondent devices 112). In some such embodiments, the biometric survey system 104 provides selectable options to the administrator device 108 (for presentation within a graphical user interface) for the survey administrator 106 to select target recipients based on categories within the response database.

For example, in some embodiments, the biometric survey system 104 provides a target-recipient menu comprising selectable options for particular respondent characteristics. For example, such selectable options may specify biographic classifications, including, but not limited to, an age classification, gender classification, geographic classification, hair-color classification, height classification, race classification, or weight classification. Additionally or alternatively, the target-recipient menu comprises selectable options that specify behavioral respondent characteristics, including, but not limited to, survey respondents' emotions, engagement levels, exercise patterns (e.g., a number of exercise-workout sessions per week, month, or year), medical appointments (e.g., number of medical appointments per week, month, or year), pharmaceuticals taken (e.g., names of prescribed pharmaceuticals), or routine biometric collections (e.g., blood-sugar measurements for diabetes). Accordingly, when performing act 214, the biometric survey system 104 optionally receives indications of selections from the target-recipient menu that define parameters for target recipients of a digital survey. The biometric survey system 104 then determines recipients to whom the digital survey will be sent based on the received parameters.

Additionally or alternatively, when performing act 214, the biometric survey system 104 provides sorting options to the administrator device 108 (for presentation within a graphical user interface) from which the survey administrator 106 may select to filter target recipients. In some such embodiments, the biometric survey system 104 sorts potential recipients by any of the response database's constituent categories (e.g., by response identifier, respondent characteristic, exercise-workout sessions or patterns). Accordingly, when performing act 214, the biometric survey system 104 optionally receives indications of selections from the sorting options and indications of a selection to distribute a digital survey to selected potential recipients from among the sorting options. The biometric survey system 104 then determines recipients to whom the digital survey will be sent based on the received indications.

After determining the recipients of a digital survey, the biometric survey system 104 performs act 216 of providing the digital survey question. For example, upon determining recipients, the biometric survey system 104 provides the digital survey question to some or all of the respondent devices 112. When performing act 216, the biometric survey system 104 may distribute a digital survey (including one or more digital survey questions) through any suitable distribution method. Such distribution methods include, but are not limited to, emails sent through the biometric survey system 104, emails sent through an external email service, a link embedded within one or more websites, a site intercept on a website (e.g., a pop-up window that includes a link to a digital survey and that is generated by the biometric survey system 104 in response to a request by the respondent client device 112a to access a web site), a post on one or more social networks (e.g., a post on a social profile or social feed), a digital survey sent through Short Message Service ("SMS") text, a digital survey sent through a mobile application, or a website or mobile application generated in response to a scan of a Quick Response ("QR") code.

As shown in FIG. 2B, after receiving the digital survey question, in one or more embodiments, the respondent devices 112 perform act 218 of capturing a response to the digital survey question and act 220 of sending the response to the digital survey question to the biometric survey system 104. As part of act 218, for example, the biometric sensor 114a of the respondent device 112a performs act 218a of capturing biometric data. In particular, act 218a includes the biometric sensor 114a capturing biometric data from the survey respondent 120a in response to a biometric query (e.g., by capturing an audio recording, heart rate, image, video, or any other biometric data).

As an optional part of act 218, the respondent device 112a performs act 218b of capturing a reply to a textual query. In particular, the respondent device 112a optionally receives user inputs from the survey respondent 120a that reply to a textual query (e.g., by receiving textual inputs or indications of selections of a choice from multiple choice answers). Upon capturing the response to the digital survey question, the respondent devices 112 send the response to the biometric survey system 104.

When performing the acts of 218 and 220, in some embodiments, the respondent device application 115a causes the respondent device 112a to associate certain biometric data with one or more replies to a textual query. To facilitate that association, the biometric survey system 104 sends a data packet comprising one or more biometric queries associated with a textual query. Such biometric queries include instructions to associate biometric data captured in response to the one or more biometric queries with the reply to the textual query. Based on the instructions from the biometric survey system 104, in some embodiments, the respondent device application 115a causes the respondent device 112a to tag the biometric data as associated with the reply to the textual query. Upon capturing the response to the digital survey question—and creating the data packet associating biometric data with a reply to a textual query—the respondent device 112a sends the data packet comprising the response to the biometric survey system 104.

As further shown in FIG. 2B, the biometric survey system 104 performs act 222 of receiving the response to the digital survey question. For instance, in some embodiments, the biometric survey system 104 receives (from the respondent device 112a) a response to the digital survey question comprising a reply to a textual query and biometric data captured by a biometric sensor in response to a biometric query. Alternatively, in some embodiments, the biometric survey system 104 receives (from the respondent device 112a) a response to the digital survey question comprising biometric data captured by the biometric sensor 114a in response to a biometric query. In some such embodiments, the response comprises biometric data captured by the biometric sensor 114*a*, but not a reply to a textual query, because the digital survey question did not comprise a textual query.

Upon receiving a response to the digital survey question, and as shown in FIG. 2B, the biometric survey system 104 performs act 224 of analyzing the biometric data, act 226 of converting the biometric data to respondent characteristic(s), and act 228 of categorizing respondent characteristic(s). In general, when performing the acts 224, 226, and 228, the question identifiers within the received data packets trigger the biometric survey system 104 to select and apply particular biometric data analyses to biometric data within the data packets. Based on that analysis, the biometric survey system 104 converts the biometric data into respondent characteristics. The biometric survey system 104 then categorizes the respondent characteristics and other information (e.g., the reply to the textual query) from the received data packets within a response database.

As suggested by FIGS. 2A and 2B, the acts 224, 226, and 228 respectively correspond to the acts 204, 206, and 208. Accordingly, the description and embodiments set forth above for the acts 204, 206, and 208 respectively apply to the acts 224, 226, 228—except that the latter acts involve a question identifier, not a response classifier, and are not necessarily part of targeting potential survey respondents. Moreover, the acts 224, 226, and 226 involve analyzing biometric data captured in response to a biometric query. Because the response received as part of act 222 comprises biometric data captured by a biometric sensor in response to a biometric query, the biometric data analyzed and converted in the acts 224 and 226 (and the respondent characteristics categorized in act 228) are associated with a questioner identifier, not a response classifier. Accordingly, a question identifier triggers the biometric survey system 104 to select and apply a biometric data analysis as part of act 224.

As shown in FIG. 2B, after analyzing and converting biometric data—and categorizing respondent characteristics—the biometric survey system 104 optionally performs act 230 of generating a report. In some embodiments, act 230 includes the biometric survey system 104 generating reports for the administrator device 108 that arrange various respondent characteristics according to responses to digital survey questions. Alternatively, in some embodiments, act 230 includes generating reports showing respondent characteristics of the survey respondents 120 for a particular digital survey—but without showing an association between the respondent characteristics and a specific digital survey question.

When performing act 230, for example, the biometric survey system 104 generates a report that indicates one or more respondent characteristics that correspond to replies by the survey respondents 120 to textual queries. In some such embodiments, the report indicates that survey respondents who provided a reply to a specific textual query have one or more respondent characteristics (e.g., by showing that survey respondents who replied to certain textual queries have respondent characteristics that correspond to categories of different emotions, respondent-engagement levels, or biographic classifications). Alternatively, in some embodiments, the report indicates that survey respondents who provided a specific reply to a specific textual query have one or more respondent characteristics (e.g., by showing survey respondents who replied with a specific answer to a textual query have respondent characteristics that correspond to categories of different emotions, respondent-engagement levels, or biographic classifications).

Additionally, when performing act 230, the biometric survey system 104 optionally generates a report that indicates one or more respondent characteristics that correspond to survey respondents who responded to one or more digital surveys. For example, the biometric survey system 104 optionally generates a report that indicates survey respondents who participated in a specific digital survey have one or more respondent characteristics. The report may indicate, for instance, that survey respondents who participated in a digital survey that collected biometric data without specifically associated textual queries have respondent characteristics that correspond to categories of different emotions, respondent-engagement levels, or biographic classifications.

In some such embodiments, the biometric survey system 104 generates a report that indicates survey respondents who participated in a specific digital survey have one or more respondent characteristics based on averages or means of particular respondent characteristics. For example, the report may show survey respondents who participated in a digital survey have respondent characteristics that correspond to categories of different emotions or respondent-engagement levels as averaged across responses to the digital survey questions of a digital survey. This disclosure describes reports in more detail below with reference to FIGS. 4 and 7.

After generating a report, and as shown in FIG. 2B, the biometric survey system 104 optionally performs act 232 of providing the report to the administrator device 108. For example, in some embodiments, the biometric survey system 104 provides the report to the administrator device 108 by emailing a digital version of the report to the administrator device 108 or by providing data that represents the report for display within a graphical user interface at the administrator device 108. Alternatively, in some embodiments, the biometric survey system 104 provides the report together with the underlying data supporting the report.

Figure 3A:
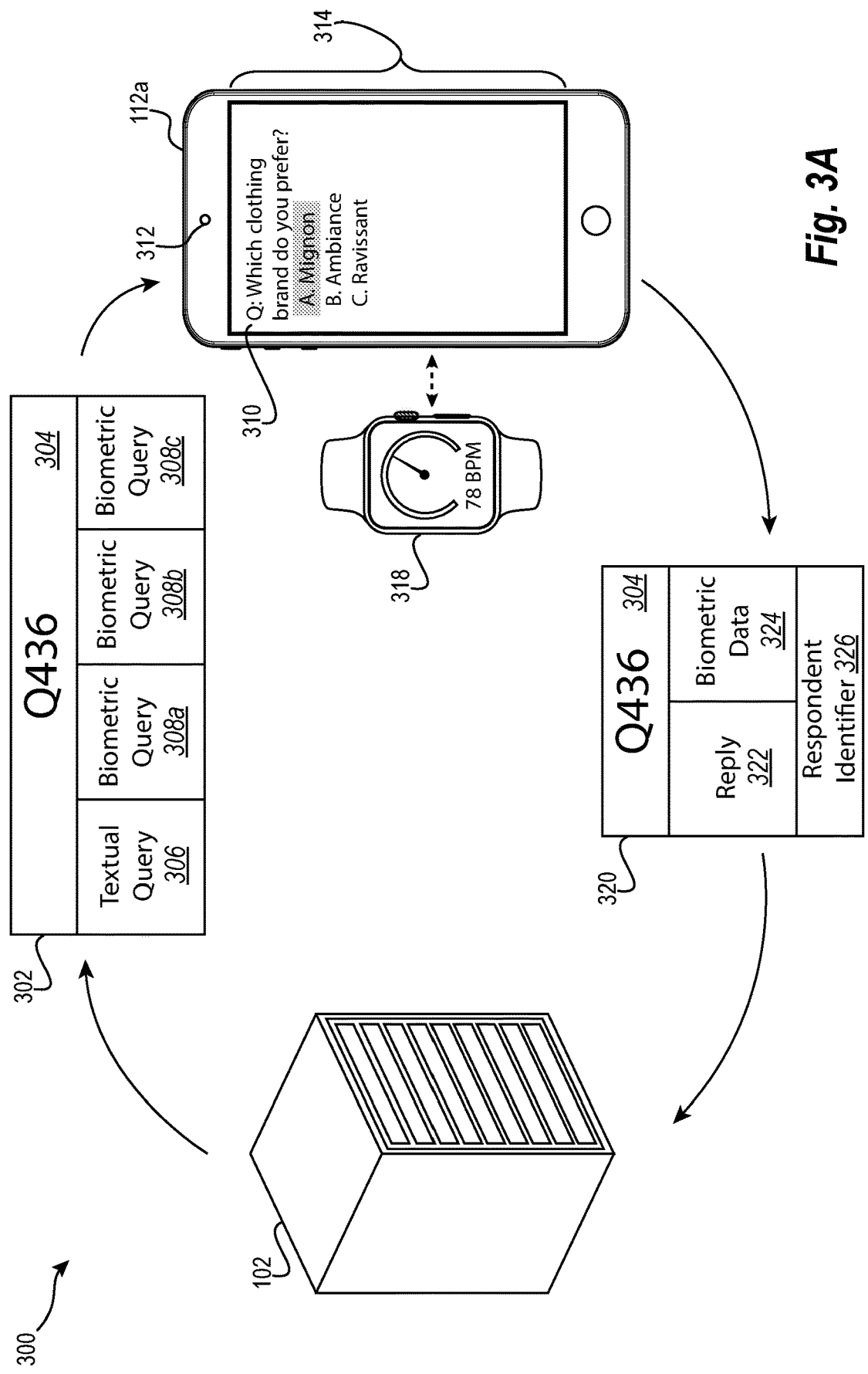
FIG. 3A illustrates a data-packet-flow diagram in accordance with one or more embodiments.
Figure 3B:
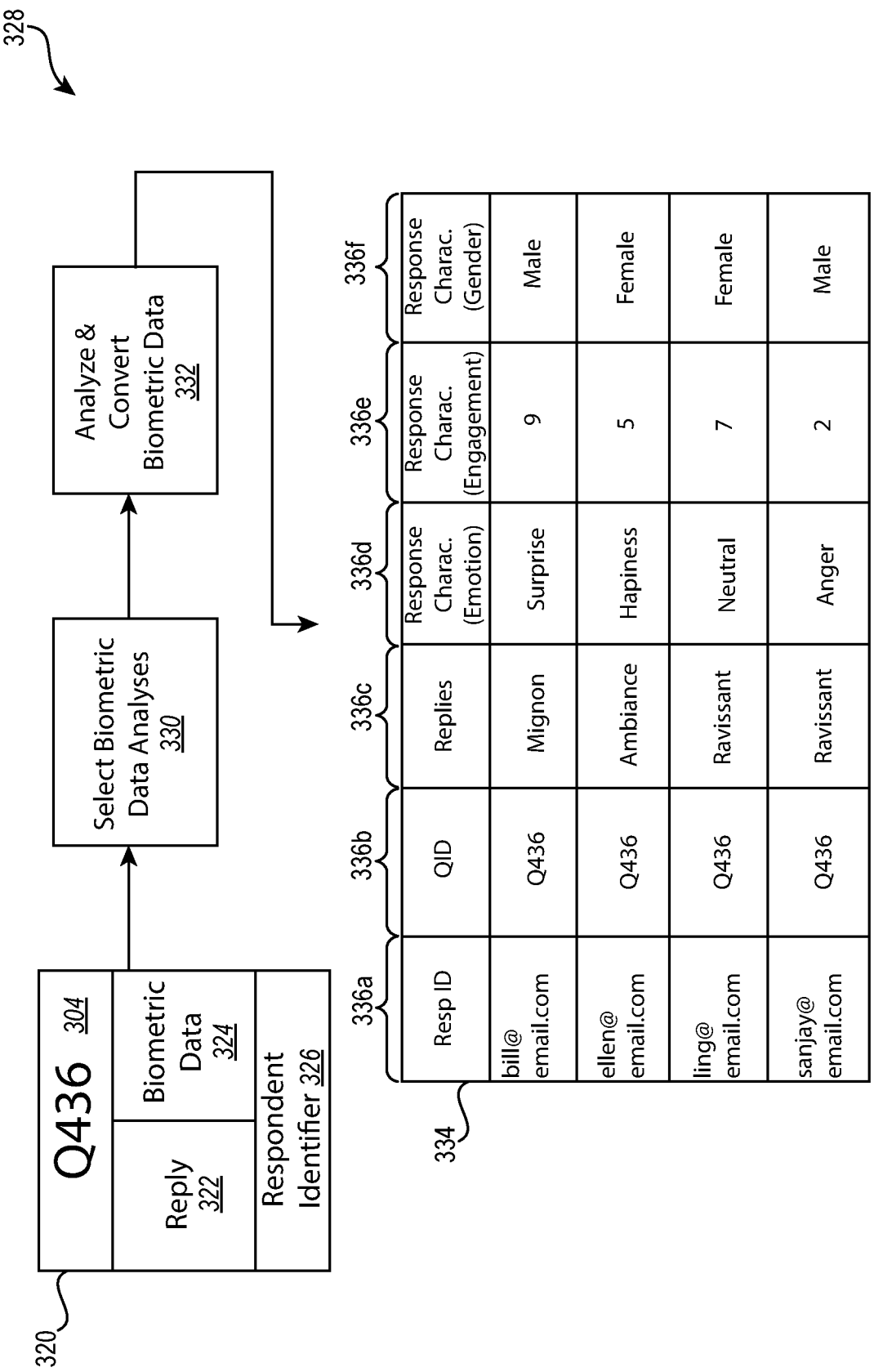
FIG. 3B illustrates respondent characteristics categorized within a response database in accordance with one or more embodiments.

Turning now to FIGS. 3A-3B, these figures depict a flow of data packets through the biometric survey system 104. FIGS. 3A-3B further include a representation of the biometric survey system 104 transmitting data packets for a digital survey and analyzing and categorizing biometric data (from the data packets) into respondent characteristics. Specifically, FIG. 3A illustrates a data-packet-flow diagram 300 of data packets transmitted to and from the server device(s) 102 and the respondent device 112*a*. FIG. 3A further depicts the contents of data packets transmitted between the server device(s) 102 and the respondent device 112*a* while the biometric survey system 104 administers a digital survey with digital survey questions. As shown in FIG. 3A, the server device(s) 102 transmit a data packet 302 to the respondent device 112*a*. After receipt of the data packet 302, and capture of the survey respondent's 120*a* response to a digital survey question, the respondent device 112*a* transmits a data packet 320 comprising the response to the server device(s) 102.

As further shown in FIG. 3A, the data packet 302 comprises components of a digital survey question. Specifically, the data packet 302 comprises a question identifier 304, a textual query 306, and biometric queries 308*a*, 308*b*, and 308*c*. Consistent with the disclosure above, the question identifier 304 provides a unique identifier for the digital survey question. The textual query 306 comprises human-readable text that poses a question for the survey respondent 120*a*. The biometric queries 308*a*, 308*b*, 308*c* each comprise a directive to the respondent device 112*a* for a biometric sensor to capture certain biometric data from the survey respondent 120*a* in association with a reply from the survey respondent 120a to the textual query. More particularly, the biometric queries 308a, 308b, and 308c each comprise computer-executable instructions that, when executed by the respondent device 112a, cause a biometric sensor to capture biometric data (e.g., while the respondent device 112a presents the textual query 306).

After receipt of the data packet 302, the respondent device 112a presents a textual question 310 within a graphical user interface 314 of the respondent device 112a. The textual question 310 is a visual representation of the textual query 306. Consistent with the disclosure above, the textual question 310 includes an interrogative sentence ("Which clothing brand do you prefer?") and multiple-choice answers ("A. Mignon," "B. Ambiance," and "C. Ravissant").

As depicted in FIG. 3A, each of the biometric queries 308a, 308b, and 308c trigger a biometric sensor to capture different biometric data in conjunction with or while the respondent device 112a presents the textual question 310 within the graphical user interface 314. For example, the biometric query 308a instructs the respondent device 112a to cause a camera 312 to capture a video of the survey respondent 120a. As an additional example, the biometric query 308b instructs the respondent device 112a to cause LED lights and photodiodes (not shown) of a synchronized watch 318 to capture a heart rate of the survey respondent 120a. As yet another example, the biometric query 308c instructs the respondent device 112a to cause a blood-pressure monitor (not shown) of the synchronized watch 318 to capture a blood-pressure measurement of the survey respondent 120a. Based on the biometric queries 308a, 308b, and 308c, the respondent device 112a causes the camera 312, the LED lights and photodiodes, and the blood-pressure monitor to respectively capture a video, heart rate, and blood pressure of the survey respondent 120a during presentation of the textual question 310.

The synchronized watch 318 provides an example of a computing device communicably synchronized with the respondent device 112a that captures and shares biometric data with the respondent device 112a. Specifically, after receiving a grant of permission from the survey respondent 120a to access biometric data, the respondent device application 115a accesses biometric data stored on the synchronized watch 318 that the LED lights, photodiodes, and blood-pressure monitor capture. As noted above, in some embodiments, biometric sensors of synchronized devices optionally capture biometric data for other software applications. Accordingly, in some embodiments, the LED lights, photodiodes, and blood-pressure monitor capture the biometric data for another software application.

As also noted above, in some embodiments, the biometric survey system 104 sends digital survey questions that comprise biometric queries without textual queries. Accordingly, in an alternative embodiment, a data packet comprises the question identifier 304 and the biometric queries 308a, 308b, and 308c, but not the textual query 306. In such an alternative embodiment, the biometric queries 308a, 308b, and 308c each trigger the capture of different biometric data during a specified period, but without the respondent device 112a presenting the textual question 310.

As further shown in FIG. 3A, after the biometric sensors capture the biometric data, the respondent device 112a generates the data packet 320 and sends the data packet 320 to the server device(s) 102. As shown, the data packet 320 represents a response to the digital survey question. Specifically, the data packet 320 comprises the question identifier 304, a reply 322 to the textual query 306, biometric data 324 captured by biometric sensors in response to the biometric queries 308a, 308b, and 308c, and a respondent identifier 326. The biometric data 324 includes data that represents the video, heart rate, and blood-pressure measurement captured by the biometric sensors described above. Consistent with the disclosure above, the respondent identifier 326 is a unique identifier for the survey respondent 120a that the biometric survey system 104 uses for processing the biometric data 324, as explained with reference to FIG. 3B.

FIG. 3B illustrates a data-flow diagram 328 that depicts the biometric survey system 104 analyzing and converting the biometric data 324 into respondent characteristics and then categorizing the respondent characteristics into a response database 334. As shown in FIG. 3B, the biometric survey system 104 performs an act 330 of selecting biometric data analyses. Specifically, the question identifier 304 triggers the biometric survey system 104 to perform act 330 of selecting specific biometric data analyses. Here, the question identifier 304 includes instructions for the biometric survey system 104 to select an emotion analysis, an engagement-level analysis, and a facial recognition algorithm that determines a gender of the survey respondent 120a.

Upon selecting specific biometric data analyses, the biometric survey system 104 performs an act 332 of analyzing and converting the biometric data 324 into respondent characteristics. As suggested by FIG. 3B, the biometric survey system 104 applies each of the selected biometric data analyses. The following paragraphs describe the analysis and conversion of the biometric data 324 according to each selected biometric data analysis. Although the following paragraphs describe the biometric data analyses in a numbered order, the biometric survey system 104 may perform the biometric data analyses and conversions described below simultaneously or in any order.

First, the biometric survey system 104 applies an embodiment of the emotion analysis to the video of the survey respondent 120a captured while the respondent device 112a presents the textual question 310. By using a facial recognition algorithm, the biometric survey system 104 scores facial features of the survey respondent 120a using FACS and determines that the survey respondent 120a expresses one of the following emotion categories: anger, contempt, fear, disgust, happiness, neutral, sadness, or surprise. As part of the analysis of act 332, the biometric survey system 104 determines a score for the facial features of the survey respondent 120a while the respondent device 112a presents the textual question 310. Here, the score corresponds to the emotion category of surprise. Based on this analysis, the biometric survey system 104 converts the video into a respondent emotion of surprise for the survey respondent 120a.

Second, the biometric survey system 104 applies an embodiment of the engagement-level analysis to the video, the heart-rate measurement, and the blood-pressure measurement captured while the respondent device 112a presents the textual question 310. Specifically, the biometric survey system 104 uses a hidden Markov model to analyze the eye movement of the survey respondent 120a in the video. Based on the hidden Markov model, the biometric survey system 104 assigns a score to the eye-movement pattern. The biometric survey system 104 further identifies a heart-rate measurement in beats per minute and a blood-pressure measurement in mmHg within the biometric data 324. Based on a comparison with previously captured heart-rate and blood-pressure measurements for the survey respondent 120a, the biometric survey system 104 assigns a score to the heart-rate measurement and a score to the blood-pressure measurement within the biometric data 324.

In this particular embodiment, the biometric survey system 104 assigns a score of 9.5 with a weight of 0.5 to the eye-movement pattern, a score of 8.5 with a weight of 0.25 to the heart-rate measurement, and a score of 8.5 with a weight of 0.25 to the blood-pressure measurement, the biometric survey system 104 determines a weighted sum of 9.0 for the various scores. Accordingly, the biometric survey system 104 converts the video, heart-rate measurement, and blood-pressure measurement from within the biometric data 324 into a respondent-engagement level of 9.0 for the survey respondent 120*a*.

Third, the biometric survey system 104 applies a facial recognition algorithm to the video that determines a gender of the survey respondent 120*a*. Specifically, the biometric survey system 104 applies a Fisherface algorithm to images of the survey respondent 120*a* from the video. Based on training the Fisherface algorithm to recognize male and female faces within images, the biometric survey system 104 determines that the survey respondent 120*a* is a male. Accordingly, the biometric survey system 104 converts the video of the survey respondent 120*a* from within the biometric data 324 into a gender classification of male.

As further shown in FIG. 3B, after converting the biometric data 324 into respondent characteristics of a respondent emotion, respondent-engagement level, and a gender classification, the biometric survey system 104 categorizes the respondent characteristics and the reply 322, among other things, within the response database 334. As presently organized, the response database 334 includes a column 336*a* for respondent identifiers, a column 336*b* for question identifiers, a column 336*c* for replies to textual queries, a column 336*d* for respondent emotion, a column 336*e* for respondent-engagement level, and a column 336*f* for gender classification. The biometric survey system 104 categorizes the information from data packet 320 within the first row of the response database 334, including categorization of the respondent characteristics converted from the biometric data 324.

As shown in the column 336*a* of FIG. 3B, the biometric survey system 104 orders the response database 334 by the respondent identifiers. Specifically, the biometric survey system 104 orders information related to different data packets (each comprising responses to digital survey questions) in descending alphabetical order by respondent identifier. As suggested above, however, the biometric survey system 104 may sort and reorder the information within the response database 334 according to the information within any of the columns 336*a*-336*f*. For example, in certain embodiments, the biometric survey system 104 sorts the information within the response database 334 in ascending or descending order of the respondent-engagement levels shown in column 336*e*.

For purposes of simplicity, FIG. 3B illustrates the response database 334 with four rows of information extracted or converted from different data packets. In some embodiments, the biometric survey system 104 categorizes information extracted or converted from any number of data packets—each comprising responses to digital survey questions—within a response database. For example, in some embodiments, a response database includes information associated with different digital survey questions (as indicated by different question identifiers) from multiple digital surveys. Although not shown, the response database 334 of FIG. 3B includes additional rows of information extracted or converted from additional data packets.

Figure 4:
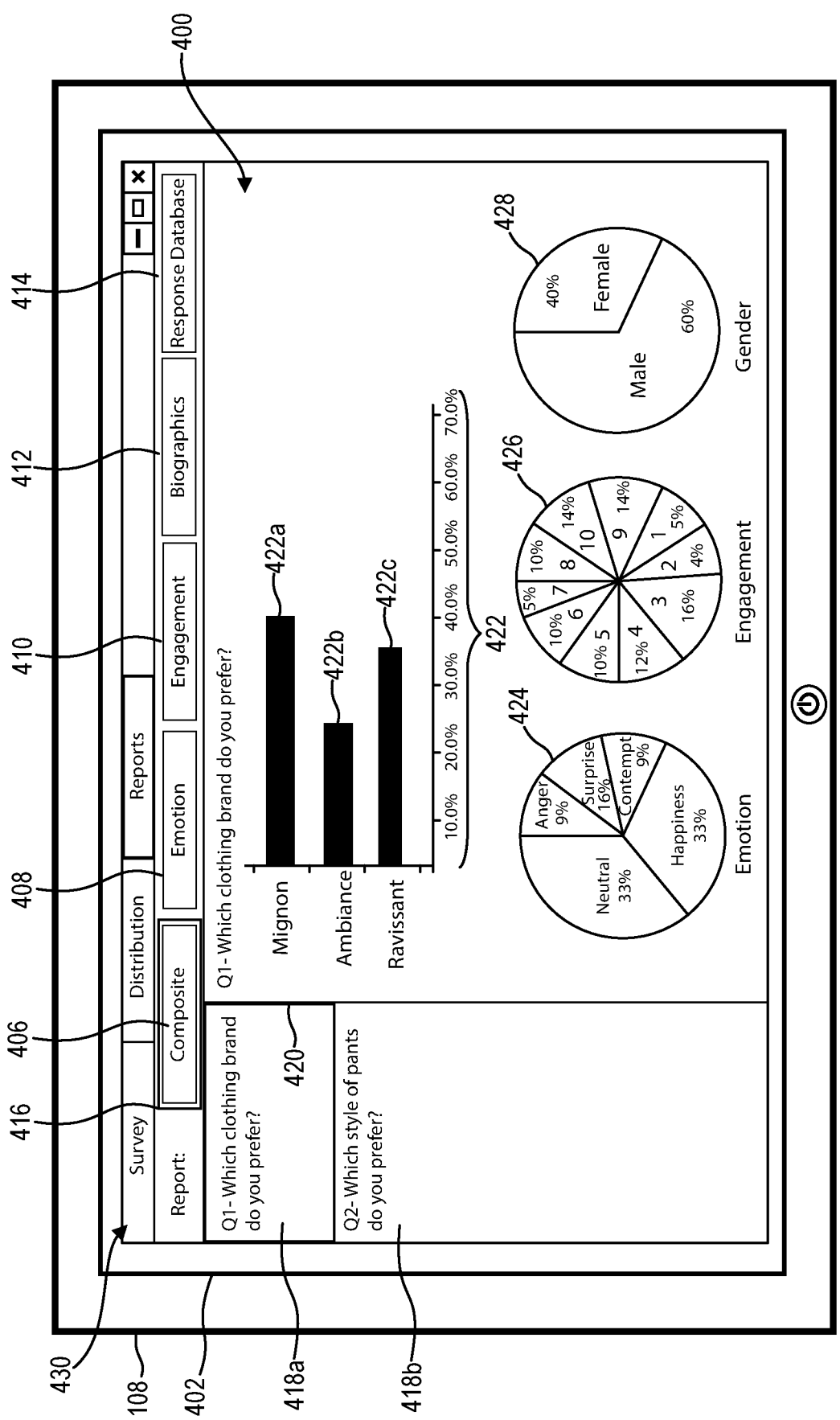
FIG. 4 illustrates a respondent-characteristic report in accordance with one or more embodiments.

As noted above, in addition to creating a response database and categorizing respondent characteristics within the database, in some embodiments, the biometric survey system 104 generates reports that comprise response information within a response database. In some such embodiments, the report identifies specific respondent characteristics that correspond to replies by one or more survey respondents to specific textual queries. FIG. 4 illustrates an embodiment of a respondent-characteristic report generated by the biometric survey system 104. As shown in FIG. 4, the biometric survey system 104 provides the respondent-characteristic report 400 for display within a graphical user interface 430. A screen 402 of the administrator device 108 in turn presents the respondent-characteristic report 400 for the survey administrator 106.

The respondent-characteristic report 400 includes a reply graph 422 that represents a collection of replies to a first textual query (i.e., "Which clothing brand do you prefer?"). FIG. 4 illustrates a representation of the first textual query as a first textual-query thumbnail 418*a*, as well as a second textual query as a second textual-query thumbnail 418*b*. As suggested by FIG. 4, the first and second textual queries are part of a single digital survey administered to multiple survey respondents. As shown, a question indicator 420 surrounds the first textual-query thumbnail 418*a* to indicate that the replies represented in the reply graph 422 are replies to the first textual query.

In addition to the reply graph 422, the respondent-characteristic report 400 further includes a respondent-emotion chart 424, a respondent-engagement-level chart 426, and a gender-classification chart 428. Each of the charts 424, 426, and 428 include a graphical representation of respondent characteristics exhibited by survey respondents while responding to the first textual query (e.g., while a respondent device presented the first textual query). By converting biometric data into respondent characteristics, as described in FIG. 3B, the biometric survey system 104 determines that survey respondents exhibited the respondent characteristics shown within the respondent-emotion chart 424, the respondent-engagement-level chart 426, and the gender-classification chart 428—while one of the respondent devices 112 presented the first textual query.

As further shown in FIG. 4, the respondent-emotion chart 424, the respondent-engagement-level chart 426, and the gender-classification chart 428 include graphical representations of respondent emotions, respondent-engagement levels, and genders exhibited by survey respondents responding to the first textual query. Specifically, the respondent-emotion chart 424 indicates that a certain percentage of survey respondents exhibited anger (9%), contempt (9%), happiness (33%), neutrality (33%), and surprise (16%). The respondent-engagement-level chart 426 indicates that a certain percentage of survey respondent exhibited a respondent-engagement level of one (5%), two (4%), three (16%), four (12%), five (10%), six (10%), seven (5%), eight (10%), nine (14%), and ten (14%). In this particularly embodiment, the respondent-engagement level of ten represents a highest respondent-engagement level, while the respondent-engagement level of one represents a lowest respondent-engagement level. Additionally, the gender-classification chart 428 indicates that a certain percentage of survey respondents were male (60%) and female (40%).

As suggested above, the biometric survey system 104 optionally generates a respondent-characteristic report that includes a response graph and respondent-characteristic chart associated with different textual queries. For example, as shown in FIG. 4, when the biometric survey system 104 receives an indication that the survey administrator 106 selects the second textual-query thumbnail 418b, the biometric survey system 104 causes the administrator device 108 to update the respondent-characteristic report 400 to include a response graph and respondent-characteristic charts associated with the second textual query.

Moreover, in addition to generating respondent-characteristic reports for different textual queries, the biometric survey system 104 optionally generates a respondent-characteristic report that includes respondent-characteristic charts associated with survey respondents who replied in a same or similar way to a textual query. For example, in some embodiments, the biometric survey system 104 generates a respondent-characteristic report that includes respondent-characteristic charts for survey respondents who selected a same answer choice for a multiple-choice question. As shown in FIG. 4, when the biometric survey system 104 receives an indication that the survey administrator 106 selects a first-answer option 422a, a second-answer option 422b, or a third-answer option 422c, the biometric survey system 104 causes the administrator device 108 to update the respondent-characteristic report 400 to include respondent-characteristic charts that represent respondent characteristics exhibited by survey respondents who selected a first answer (i.e., "A. Mignon"), a second answer (i.e., "B. Ambiance"), or a third answer (i.e., "C. Ravissant"), respectively.

In addition to generating respondent-characteristic reports for survey respondents answering in the same way, the biometric survey system 104 provides selectable options to generate a respondent-characteristic report showing different respondent characteristics in isolation. As shown in FIG. 4, for example, the respondent-characteristic report 400 includes a composite-report option 406, a respondent-emotion-report option 408, an engagement-level-report option 410, and a biographic-report option 412. A report indicator 416 surrounds the composite-report option 406 to indicate that the respondent-characteristic report 400 currently includes a composite of different respondent characteristics. Each of the charts 424, 426, and 428 represent the different respondent characteristics.

When the biometric survey system 104 receives an indication that the survey administrator 106 selects the respondent-emotion-report option 408, the engagement-level-report option 410, or the biographic-report option 412, however, the biometric survey system 104 updates the respondent-characteristic report 400 to include data corresponding to a respondent emotion, respondent-engagement level, or demographic classification, respectively. But in each case, the updated respondent-characteristic report shows data representing a single respondent characteristic. For example, the respondent-emotion-report option 408 triggers the biometric survey system 104 to update the respondent-characteristic report 400 to include the respondent-emotion chart 424 without the respondent-engagement-level chart 426 or the gender-classification chart 428.

Additionally, in some embodiments, the biometric survey system 104 generates a report that depicts a response database for a digital survey. In such embodiments, and as described above, the response database is sortable by any category. As shown in FIG. 4, for example, the respondent-characteristic report 400 includes a response-database-report option 414. When the biometric survey system 104 receives an indication that the survey administrator 106 selects the response-database-report option 414, the biometric survey system 104 generates a report showing a response database that categorizes the underlying response data for a digital survey. For example, upon receiving an indication that the survey administrator 106 selects the response-database-report option 414, the biometric survey system 104 optionally generates a respondent-characteristic report with a graphical representation of the response database 334 of FIG. 3B.

Figure 5A:
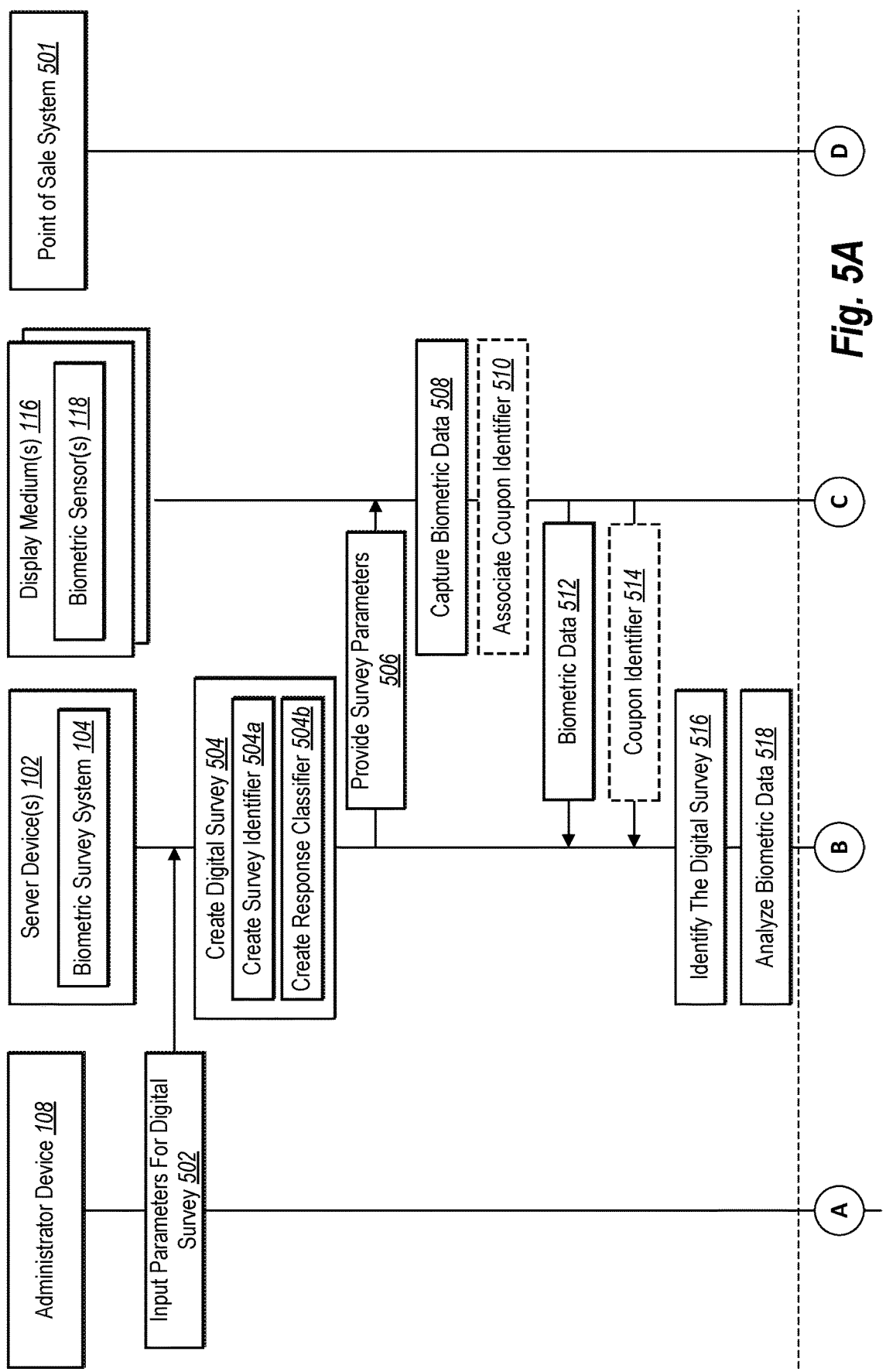
FIGS. 5A-5B illustrate a sequence-flow diagram of converting biometric data into respondent characteristics associated with respondents who interact with display mediums in accordance with one or more embodiments.
Figure 5B:
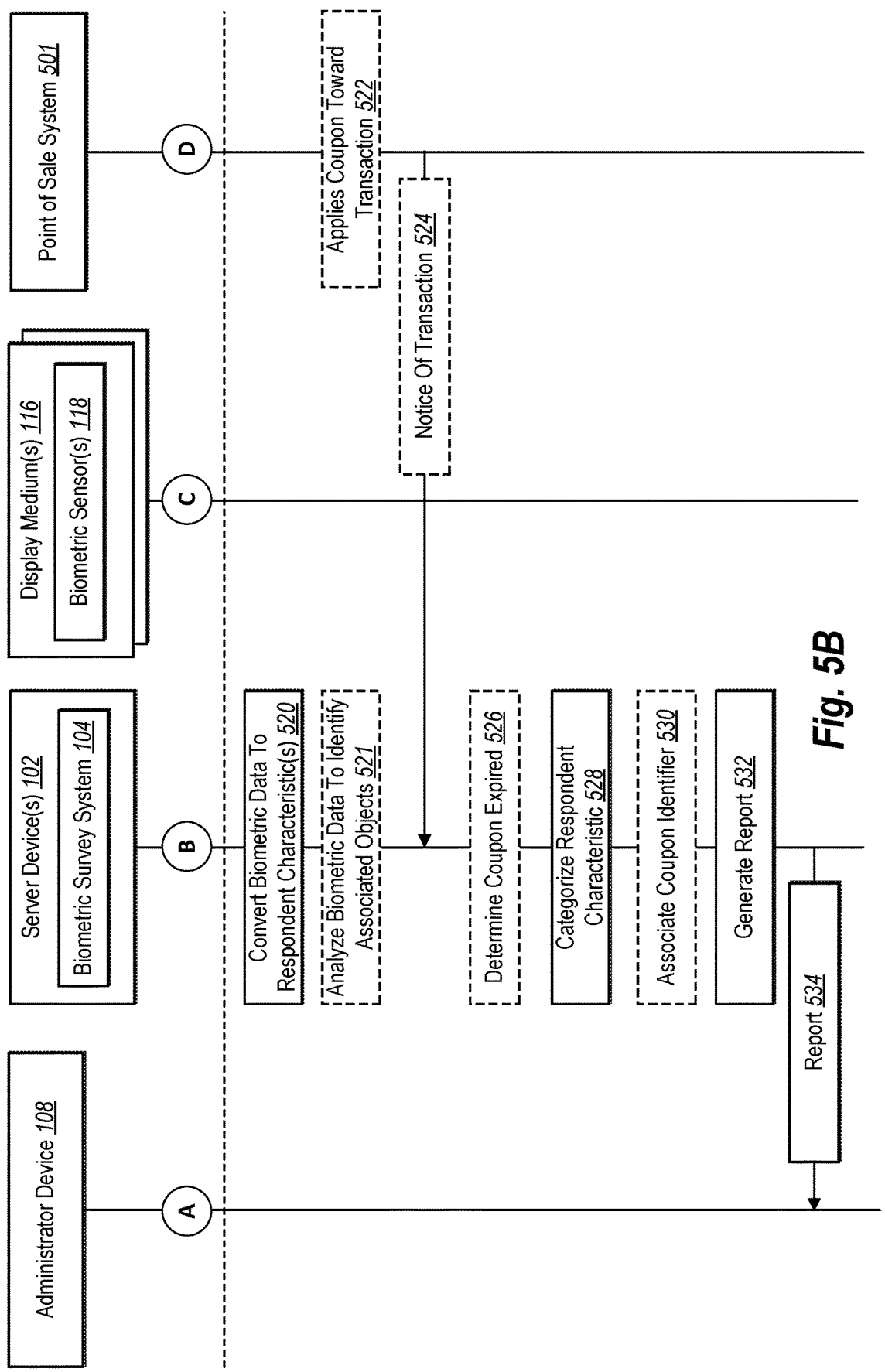

Turning now to FIGS. 5A-5B, these figures provide an overview of embodiments of the biometric survey system 104 that administer digital surveys to respondents who interact with a display medium to collect and convert biometric data into respondent characteristics for categorization within a response database. Specifically, FIGS. 5A-5B illustrate a representation of a sequence of acts 502-534 that the server device(s) 102, the administrator device 108, the display mediums 116, or a point-of-sale system 501 perform to, among other things, collect biometric data from survey respondents who interact with a display medium and convert the biometric data into respondent characteristics for categorization within a response database. For instance, in some embodiments, the server device(s) 102, administrator device 108, display mediums 116, or point-of-sale system 501 include computer-executable instructions that, when executed by a processor thereon, cause the server device(s) 102, administrator device 108, display mediums 116, or point-of-sale system 501 to perform one or more of the acts 502-534 shown in FIGS. 5A-5B.

For ease of reference, the following paragraphs describe the biometric survey system 104 as performing one or more of the acts 502-534 rather than any particular device. As suggested above, the biometric survey system 104 comprises computer-executable instructions that cause the server device(s) 102, a client device (e.g., administrator device 108), or the display mediums 116 to perform one or more of the acts 502-534. Rather than repeatedly describe the relationship between the instructions within the biometric survey system 104, on the one hand, and the various devices, on the other hand, this disclosure will describe the biometric survey system 104 as performing the acts as a shorthand for that relationship. Additionally, in some embodiments, the display mediums 116 are not computing devices, but are associated with computing devices that perform one or more of act 502-534. Although the following paragraphs primarily refer to the display mediums 116 performing certain acts, in some embodiments, the associated computing devices perform the specified acts.

Turning back now to the acts 502-534, as shown in FIG. 5A, the administrator device 108 performs act 502 of receiving and sending input parameters for a digital survey. As noted above, the biometric survey system 104 provides tools to the administrator device 108 for the survey administrator 106 to compose a digital survey for a display medium. To facilitate the composition of such digital surveys, the biometric survey system 104 provides tools, selectable options, and/or menus within a graphical user interface to compose a digital survey that optionally concerns one or more digital content items and comprises response classifiers and survey identifiers, among other things.

For example, in some embodiments, the biometric survey system 104 provides a digital survey template to the administrator device 108 for presentation within a graphical user interface. In such embodiments, the digital survey template comprises a digital space in which the survey administrator 106 may specify, edit, and/or otherwise create one or more survey identifiers or response classifiers for use with a display medium or upload digital content items for presentation on a display medium.

As part of the digital survey template, in some embodiments, the biometric survey system 104 provides input options for a survey identifier. For example, as part of act 502 in FIG. the biometric survey system 104 provides to the administrator device 108 selectable options or a field (for presentation within the graphical user interface) to identify a display medium with which survey respondents may interact for the digital survey. Accordingly, when the administrator device 108 receives input parameters for a digital survey, the input parameters include an identification by Internet Protocol ("IP") address, Global Position System ("GPS") coordinates, physical address or location, or some other location of a display medium. The biometric survey system 104 later creates a survey identifier based on the location of the identified display medium.

In addition to providing input options for a survey identifier, in some embodiments, the biometric survey system 104 provides to the administrator device 108 selectable options (for presentation within the graphical user interface) to include data objects within a response classifier that specify a type of biometric data for the digital survey. The data objects may specify, for example, that data packets of biometric data include (or may include) an audio recording, image, video, or some other biometric data. Once biometric sensors from a display medium capture the relevant biometric data, the data objects within the response classifier specify that the biometric data includes a specific type of biometric data.

Similarly, in certain embodiments, the biometric survey system 104 provides a field (for presentation within the graphical user interface) in which the survey administrator 106 may input instructions, code, or other information specifying a type of biometric data for the digital survey. Regardless of whether the biometric survey system 104 uses selectable options, fields, or some other input option, the data objects for a response classifier indicate that the digital survey collects—and that data collected for the digital survey include (or may include)—a specific type of biometric data.

In addition (or in the alternative) to response classifiers with such data objects, in some embodiments, the response classifier further includes capture instructions for a display medium (or a computing device associated with a display medium) to cause a biometric sensor to capture a specific type of biometric data. Conversely, the response classifier optionally identifies the biometric data that a biometric sensor of the display medium captures independent of such capturing instructions from the biometric survey system 104.

Similarly, in addition to providing input options for a response classifier and survey identifier, the biometric survey system 104 optionally provides attachment options for a digital content item. Such digital content items may be attached for presentation by the display medium. For example, as part of act 502 of FIG. 5A, the biometric survey system 104 provides to the administrator device 108 selectable attachment options or a field (for presentation within the graphical user interface) to identify and attach a digital content item for presentation on a display medium. In some such embodiments, the administrator device 108 receives an identification of a digital-image file or digital-video file for a smart television (or other display medium) to present on a screen. One such embodiment is described below with reference to FIG. 6A.

After receiving input parameters for a digital survey, and as part of act 502, the administrator device 108 sends (and the biometric survey system 104 receives) the input parameters that form the basis for the digital survey. Based on the received input parameters, the biometric survey system 104 performs act 504 of creating a digital survey for a display medium. When performing this act, the biometric survey system 104 generates a digital file that includes each of the received input parameters. This digital file specifies a display medium and the biometric data to be collected from survey respondents who interact with the display medium. The digital file also optionally specifies the digital content items that the display medium shall present.

As indicated by FIG. 5A, in addition to creating such a digital file, act 504 includes the biometric survey system 104 creating data packets that include information specifying, among other things, the biometric data to be collected from a display medium and return instructions to send the collected biometric data back to the biometric survey system 104. When doing so, the biometric survey system 104 performs act 504a of creating a survey identifier. As suggested above, the survey identifier may comprise an alphanumeric sequence, code, or other information that uniquely identifies the digital survey. In some cases, the survey identifier may identify a digital survey associated with a particular display medium. Alternatively, the survey identifier may identify a digital survey associated with a particular digital content item displayed by a particular display medium. In some embodiments, the biometric survey system 104 attaches the survey identifier to both the digital file described above and to data packets distributed to display mediums.

When performing act 504, the biometric survey system 104 also performs act 504b of creating one or more response classifiers. As suggested above, such response classifiers comprise data objects that specify data packets may comprise a specific type of biometric data. In some such embodiments, the response classifier also includes capture instructions for a display medium (or a computing device associated with a display medium) to cause a biometric sensor to capture specific biometric data. Similar to the survey identifier, in some embodiments, the biometric survey system 104 attaches the response classifiers to both the digital file described above and to data packets distributed to display mediums.

As part of act 504 in FIG. 5A, in addition to creating a survey identifier and one or more response classifiers, the biometric survey system 104 creates a data packet. This data packet comprises, among other things, the survey identifier, the one or more response classifiers, and return instructions to send collected biometric data back to the biometric survey system 104. In some embodiments, the return instructions comprise a data object that specifies an IP address for the server device(s) 102. In some instances, the return instructions further comprise computer-executable return instructions that, when executed by the display medium 116a, cause the display medium 116a to send a data packet comprising a survey identifier, one or more response classifiers, and biometric data captured by biometric sensors to the server device(s) 102. Alternatively, a computing device associated with the display medium 116a executes the return instructions and sends the data packet to the server device(s) 102.

In some embodiments, the return instructions further specify that the display medium 116a (or the computing device associated with the display medium 116a) send data packets after each discrete capture of biometric data. For example, the return instructions may specify to send data packets after a camera captures each image each video of a predetermined duration. The return instructions may further specify a delivery schedule for sending such data packets. This disclosure describes additional embodiments of such data packets below with reference to FIG. 6A.

As shown in FIG. 5A, after creating a digital survey, the biometric survey system 104 performs act 506 of providing survey parameters to the display mediums 116. In some such embodiments, the biometric survey system 104 sends the data packets created as part of act 504 to the display mediums 116. Alternatively, the biometric survey system 104 sends the data packets created as part of act 504 to computing devices associated with one or more of the display mediums 116. These data packets serve as the vehicles through which the biometric survey system 104 distributes and administers a digital survey for a display medium.

As further depicted in FIG. 5A, after the display mediums 116 receive the survey parameters, the biometric sensors 118 of the display mediums 116 perform act 508 of capturing biometric data. For example, in some embodiments of act 508, the biometric sensor 118a captures biometric data from the survey respondent 122a as she interacts with the display medium 116a. For instance, the biometric sensor 118a captures biometric data from the survey respondent 122a as she views, ignores, walks past, touches, pushes, or pulls the display medium 116a or alternatively samples or tries on items associated with the display medium 116a. While the survey respondent 122a interacts in any such way with the display medium 116a, the biometric sensor 118a captures an audio recording, image, or video of the survey respondent 122a, or some other biometric data from the survey respondent 122a.

As noted above, in some embodiments, a survey respondent 122 may interact with a display medium by taking a coupon from the display medium. As shown in FIG. 5A, in some such embodiments, the display mediums 116 optionally performs act 510 of associating a coupon identifier with each coupon taken by the survey respondents 122. The term "coupon identifier" refers to a unique alphanumeric sequence, barcode, code, number, Quick Response ("QR") code, or other identifier associated with a given coupon.

For example, in some embodiments, the display mediums 116 generate a coupon identifier for each coupon taken by one of the survey respondents 122 as they interact with the individual display mediums 116. Alternatively, in some embodiments, the display mediums 116 receive and follow associating instructions from the biometric survey system 104 to associate a pre-generated coupon identifier with a coupon taken by one of the survey respondents 122. In some such embodiments, the biometric survey system 104 generates or associates the coupon identifiers and sends the coupon identifiers to the display mediums 116 within a data packet.

By associating the coupon identifiers with coupons—or receiving such coupon identifiers—the biometric survey system 104 facilitates the tracking of a coupon's redemption or expiration. As disclosed further below, the coupon identifiers enable the biometric survey system 104 to correlate certain respondent characteristics with the redemption or expiration of that coupon within a response database. By drawing such correlations, the biometric survey system 104 differentiates between the respondent characteristics of the survey respondents 122 who took and redeemed a coupon with a transaction, on the one hand, and the respondent characteristics of the survey respondents 122 who took but did not redeem a coupon with a transaction.

As further shown in FIG. 5A, after capturing the biometric data and/or associating a coupon identifier with a coupon, the display mediums 116 perform act 512 of sending the biometric data to the biometric survey system 104. In particular, the display mediums 116 (or associated computing devices) send data packets that comprise, among other things, biometric data, a survey identifier, one or more response classifiers, and a respondent identifier. As explained below, certain components of the data packet trigger the biometric survey system 104 to apply particular biometric data analyses to the biometric data and—based on that analysis—convert the biometric data into respondent characteristics.

Additionally, the biometric survey system 104 optionally performs act 514 of sending the coupon identifier to the biometric survey system 104. When doing so, the display mediums 116 (or associated computing devices) send data packets that further comprise a coupon identifier to the biometric survey system 104.

As further shown in FIG. 5A, after receiving the biometric data and/or coupon identifiers, the biometric survey system 104 performs act 516 of identifying the digital survey. For example, based on the survey identifier within a received data packet, the biometric survey system 104 identifies the digital survey created above. Specifically, the biometric survey system 104 identifies the digital file that specifies the display medium and the biometric data to be collected for the digital survey. This digital file includes the information necessary to administer the digital survey and process data packets received as part of the digital survey.

As shown in FIGS. 5A-5B, after identifying the digital survey, the biometric survey system 104 performs act 518 of analyzing the biometric data and act 520 of converting the biometric data to respondent characteristic(s). In general, when performing the acts 518 and 520, the response classifiers within the received data packets trigger the biometric survey system 104 to select and apply particular biometric data analyses to biometric data within the data packets. Based on that analysis, the biometric survey system 104 converts the biometric data into respondent characteristics.

As suggested by FIGS. 5A and 5B, the acts 518 and 520 respectively correspond to the acts 204 and 206 of FIG. 2A. Accordingly, the description and embodiments set forth above for the acts 204 and 206 of FIG. 2A respectively apply to the acts 518 and 520 of FIGS. 5A and 5B—except that the latter acts involve one or more response classifiers, not a question identifier, and are not necessarily part of targeting potential survey respondents. Because the data packets received as part of act 512 comprise biometric data captured by biometric sensors 118 of the display mediums 116, the biometric data analyzed and converted in the acts 518 and 520 are associated with a response classifier, not a question identifier. Accordingly, a response classifier triggers the biometric survey system 104 to select and apply a biometric data analysis as part of act 518.

Besides analyzing and converting biometric data, the biometric survey system 104 optionally performs act 521 of analyzing biometric data to identify associated objects. In such embodiments, the biometric survey system 104 applies object detection algorithms to identify objects within an image or video from within the received biometric data. When doing so, the biometric survey system 104 may apply any well-known object detection algorithms to identify objects within an image or video. In performing act 521, the biometric survey system 104 detects objects associated with a survey respondent, such as objects the survey respondent is carrying or wearing (e.g., bags, phones, watches) or objects accompanying the survey respondent (e.g., children, cats, dogs, pets).

For example, in some embodiments, the biometric survey system 104 applies appearance-based methods of object detection, such as edge matching, divide-and-conquer searching, greyscale matching, gradient matching, histograms of receptive field responses, or feature-based methods of object detection, such as interpretation trees, pose consistency, pose clustering, invariance, Gradient Location and Orientation Histogram ("GLOH"), geometric hashing, Histogram of Oriented Gradients ("HOG"), Phase Stretch Transform ("PST"), Scale-Invariant Feature Transform ("SIFT"), and Speeded Up Robust Features ("SURF").

As further shown in FIG. 5B, in addition to the biometric survey system 104 analyzing and converting biometric data to respondent characteristics, the point-of-sale system 501 optionally performs act 522 of applying a coupon toward a transaction and act 524 of sending a notice of the transaction to the biometric survey system 104. In some embodiments, the point-of-sale system 501 comprises a computing device that processes transactions, a barcode scanner, and a card reader, among other things, located at a brick-and-mortar facility. Alternatively, in some embodiments, the point-of-sale system 501 comprises a computing device that processes transactions over a network, such as server device(s) that process an electronic-commerce transaction over the Internet.

When performing act 522, the point-of-sale system 501 applies a coupon taken by one of the survey respondents 122 from one of the display mediums 116 toward a transaction. In such transactions, a customer redeems the coupon as part of a purchase of an item at a reduced price or as part of a purchase of an item at no cost to the customer. In some embodiments, the customer is one of the survey respondents 122 who took a coupon from one of the display mediums 116.

When performing act 524, the point-of-sale system 501 sends a notice to the biometric survey system 104 that includes a coupon identifier for a coupon that was redeemed as part of a transaction. For example, the point-of-sale system 501 optionally sends data representing the coupon identifier, item purchased, and date and time of transaction as the notice. Additionally or alternatively, in some embodiments, the point-of-sale system 501 sends data indicating that a coupon associated with a coupon identifier was redeemed.

As indicated above, in some cases, the biometric survey system 104 does not receive a notice that a particular coupon has been redeemed. Instead, the biometric survey system 104 optionally performs act 526 of determining that a coupon expired. In such embodiments, the coupon identifiers include an expiration date for coupons taken by one of the survey respondents 122 from one of the display mediums 116. Accordingly, the biometric survey system 104 determines that a coupon taken by the survey respondent 122a from the display medium 116a has expired without a corresponding transaction in which the coupon was redeemed.

Alternatively, when coupon identifiers lack an expiration date, the biometric survey system 104 determines that a coupon taken by one of the survey respondents 122 from one of the display mediums 116 has not been redeemed within a predetermined time (e.g., three months, one year). In such embodiments, the biometric survey system 104 determines or marks within a respondent database that the biometric survey system 104 has not received notice that a coupon associated with a coupon identifier has been redeemed.

As shown in FIG. 5B, in addition to converting biometric data and optionally processing information associated with coupon identifiers, the biometric survey system 104 performs act 528 of categorizing respondent characteristic(s). In general, when performing the 528, the biometric survey system 104 categorizes respondent characteristics and other information from received data packets within a response database. As suggested by FIG. 5B, act 528 corresponds to act 208 of FIG. 2A. Accordingly, the description and embodiments set forth above for act 208 of FIG. 2A apply to act 528 of FIG. 5B.

In addition to categorizing response characteristics within a response database, the biometric survey system 104 optionally performs act 530 of associating a coupon identifier and transactional information with respondent characteristics within a response database. As part of categorizing information within a response database, the biometric survey system 104 associates a coupon identifier with information concerning a coupon-redeeming transaction or with information concerning no coupon-redeeming transaction. In making such associations, the biometric survey system 104 tracks whether a coupon associated with a coupon identifier has been redeemed or expired within a response database and associates that information with respondent characteristics of a survey respondent who took a particular coupon.

For example, in some embodiments, after receiving notice that a coupon was redeemed as part of a transaction, the biometric survey system 104 associates a coupon identifier for that coupon and an identification of the transaction within a response database. The biometric survey system 104 then associates the coupon identifier and the identification of the transaction with respondent characteristics within the response database. When doing so, the biometric survey system 104 categorizes the identification of the transaction with other information related to the survey respondent who took the redeemed coupon within the response database. In some such embodiments, the biometric survey system 104 inputs an indicator within the response database that a respondent redeemed a coupon associated with a particular coupon identifier.

Conversely, in some embodiments, after determining that a coupon has expired, the biometric survey system 104 associates a coupon identifier for that coupon and an indication of no corresponding transaction within the response database. The biometric survey system 104 then associates the coupon identifier and indication of no corresponding transaction with respondent characteristics within the response database. When doing so, the biometric survey system 104 categorizes the indication of no corresponding transaction with other information related to the survey respondent who took the unredeemed coupon within the response database. In some such embodiments, the biometric survey system 104 inputs an indicator within the response database that a coupon associated with a particular coupon identifier has expired or has otherwise yet to be redeemed.

As further shown in FIG. 5B, after categorizing respondent characteristics and optionally associating coupon identifiers within transaction information, the biometric survey system 104 optionally performs act 532 of generating a report. In some embodiments, when performing act 532, the biometric survey system 104 generates a report for the administrator device 108 that arranges various respondent characteristics according to individual survey respondents 122 who interacted with one of the display mediums 116. Alternatively, in some embodiments, the biometric survey system 104 generates a report that arranges various respondent characteristics according to individual survey respondents 122 who interacted with a particular digital content item presented on one of the display mediums 116.

When performing act 532, for example, the biometric survey system 104 generates a report that indicates one or more respondent characteristics that correspond to all the survey respondents 122 who interacted with the display medium 116a or a digital content item presented by the display medium 116a. Alternatively, in some embodiments, the report indicates respondent characteristics of the survey respondents 122 who interacted with the display medium 116a and who have a particular respondent characteristic.

Additionally, when performing act 532, the biometric survey system 104 optionally generates a report that indicates one or more respondent characteristics that correspond to the survey respondents 122 who interacted with a same digital content item presented on different display mediums 116. Conversely, the biometric survey system 104 optionally generates a report that indicates one or more respondent characteristics that correspond to the survey respondents 122 who interacted with different digital content items presented on a single display medium, such as the display medium 116a.

In some such embodiments, the biometric survey system 104 generates a report that indicates the survey respondents 122 who interacted with one of the display mediums 116 with one or more respondent characteristics based on averages or means of particular respondent characteristics. For example, the report may show survey respondents 122 the survey respondents 122 who interacted with one of the display mediums 116 have respondent characteristics that correspond to categories of different emotions or respondent-engagement levels as averaged across responses to the digital survey questions of a digital survey. This disclosure describes reports in more detail below with reference to FIG. 7.

After generating a report, and as shown in FIG. 5B, the biometric survey system 104 optionally performs act 534 of providing the report to the administrator device 108. For example, in some embodiments, the biometric survey system 104 provides the report to the administrator device 108 by emailing a digital version of the report to the administrator device 108 or by providing data that represents the report for display within a graphical user interface of the administrator device 108. Alternatively, in some embodiments, the biometric survey system 104 provides the report together with the underlying data supporting the report.

Figure 6A:
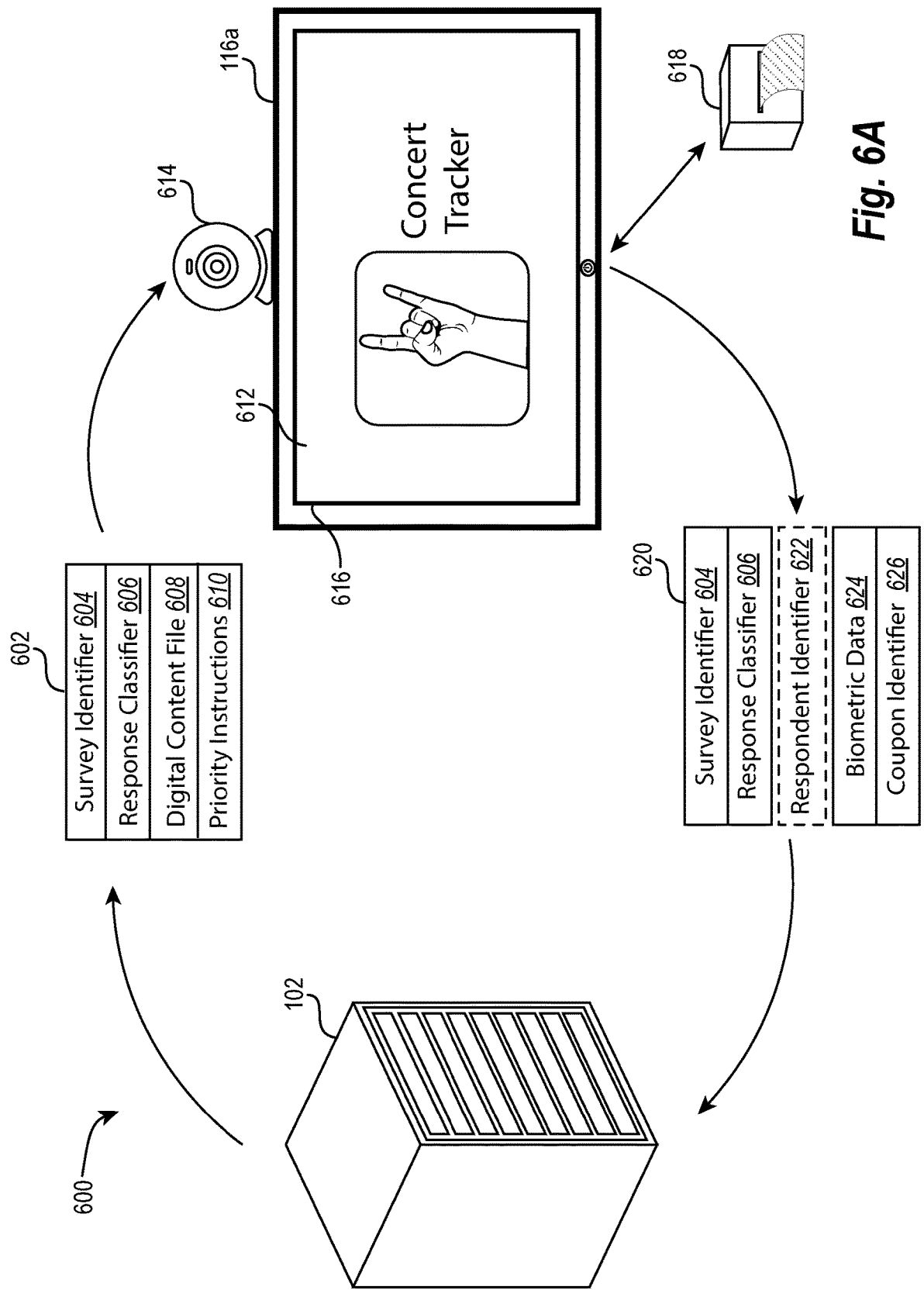
FIG. 6A illustrates a data-packet-flow diagram in accordance with one or more embodiments.
Figure 6B:
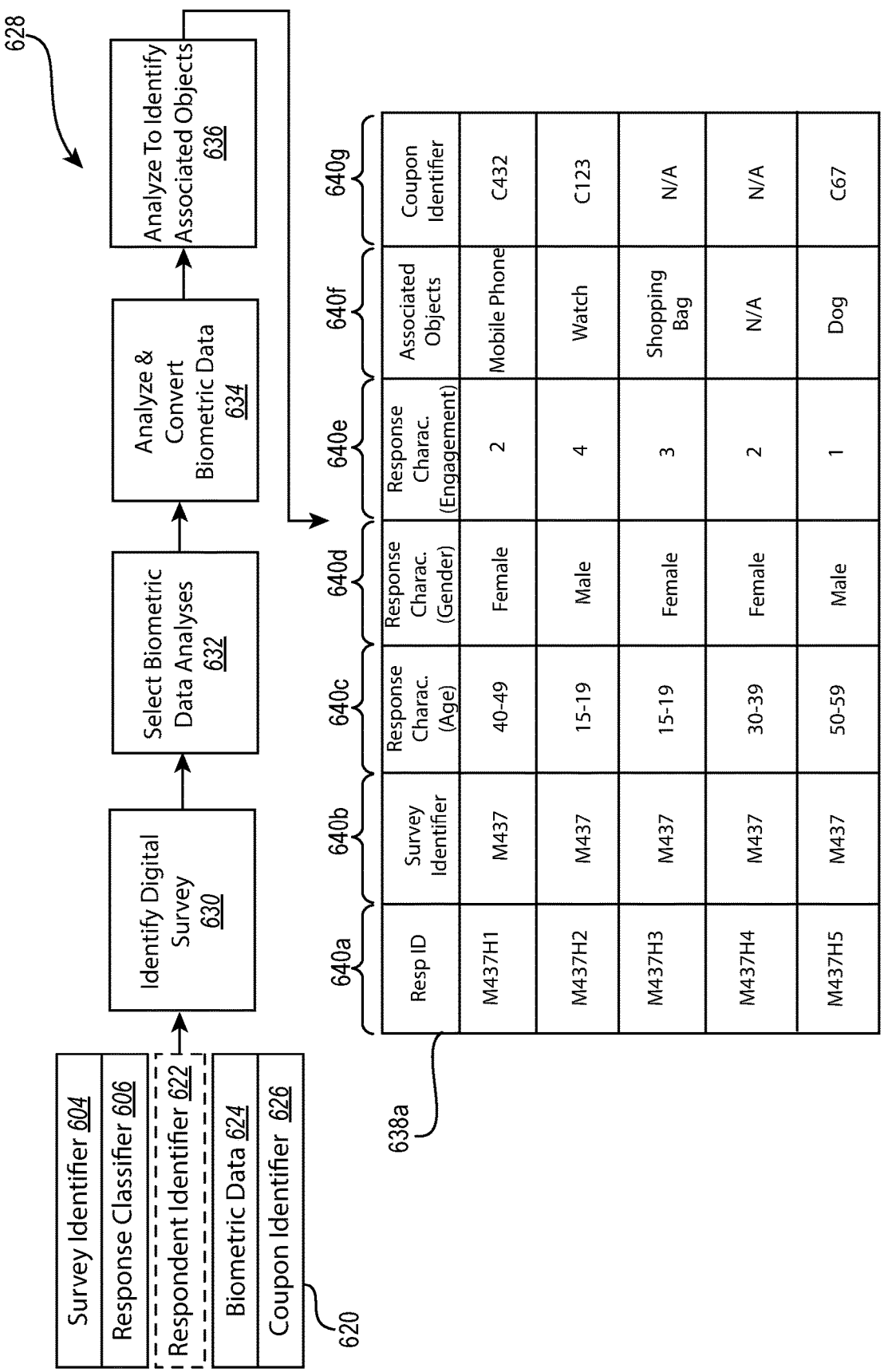
FIG. 6B illustrates respondent characteristics categorized within a response database in accordance with one or more embodiments.
Figure 6C:
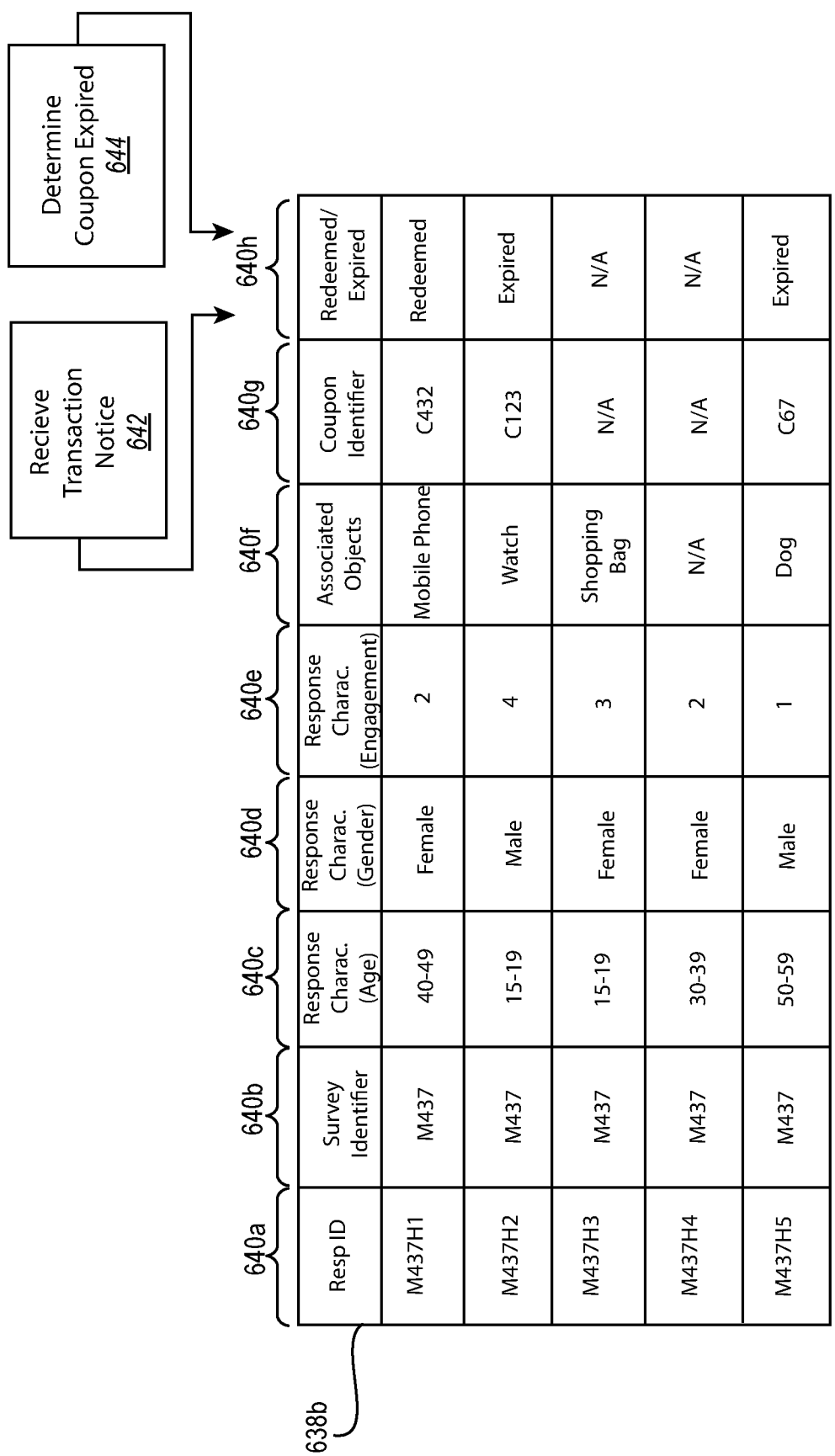
FIG. 6C illustrates an updated response database in accordance with one or more embodiments.

Turning now to FIGS. 6A-6C, these figures depict a flow of data packets through the biometric survey system 104. FIGS. 6A-6C further include a representation of the biometric survey system 104 transmitting data packets associated with a digital survey for a display medium and analyzing and categorizing biometric data (from the data packets) into respondent characteristics. Specifically, FIG. 6A illustrates a data-packet-flow diagram 600 of data packets transmitted to and from the server device(s) 102 and the display medium 116a. In the embodiments depicted by FIG. 6A, the display medium 116a comprises a smart television connected to the network 110. Accordingly, the display medium 116a may transmit and receive data packets and present different digital content items from within the data packets.

FIG. 6A further illustrates the contents of data packets transmitted between the server device(s) 102 and the display medium 116a in the process of the biometric survey system 104 administering a digital survey. As shown, the server device(s) 102 transmit a data packet 602 to the display medium 116a. After receipt of the data packet 602 and capture of the biometric data, the display medium 116a transmits a data packet 620 comprising the biometric data to the server device(s) 102.

As further shown in FIG. 6A, the data packet 602 comprises survey parameters. Specifically, the data packet 602 comprises a survey identifier 604, a response classifier 606, a digital-content file 608, and priority instructions 610. Consistent with the disclosure above, the survey identifier 604 provides a unique identifier for a digital survey associated with the display medium 116a. Additionally, and as shown here, the survey identifier 604 identifies a digital content item for display on the display medium 116a.

Relatedly, the response classifier 606 indicates a type of biometric data collected for the digital survey associated with the display medium 116a. In this particular embodiment, the response classifier 606 also comprises capture instructions for the display medium 116a to cause a camera to capture video clips of the survey respondents 122 interacting with the display medium 116a. More specifically, the capture instructions specify that the camera capture video clips of the survey respondents 122 interacting with a particular digital content item (e.g., when walking by or viewing the display medium 116a).

The digital-content file 608 in turn comprises the digital content item to be presented on the display medium 116a. In this case, the digital content item comprises a digital advertisement. Relatedly, the priority instructions 610 include commands that control the priority or ratio at which the display medium 116a presents the digital content item. For example, the priority instructions 610 may specify that the display medium 116a present the digital content item a certain number of times an hour or other time increment, according to a ratio relative to other digital content items (e.g., once every certain number of digital content items), or according to some other schedule.

After receipt of the data packet 602, the display medium 116a presents a digital content item 612 within a display screen 616 of the display medium 116a. As indicated above, the display medium 116a presents the digital content item 612 according to the priority instructions 610. Although FIG. 6A illustrates the digital content item 612 as an image comprising a mobile application advertisement, the digital content item 612 may be any digital content item. Additionally, although not shown in FIG. 6A, the display medium 116a presents additional content items, such as additional content items received from the server device(s) 102.

As further depicted in FIG. 6A, the response classifier 606 triggers a biometric sensor to capture certain biometric data while the display medium 116a presents the digital content item 612 within the display screen 616. Specifically, the capture instructions of the response classifier 606 instruct the display medium 116a to cause a camera 614 to capture a video clip of the survey respondents 122 as they interact with the display medium 116a. In some embodiments, the capture instructions instruct the camera 614 to capture a video clip repeatedly or when one of the survey respondents 122 is within a certain depth of the display medium 116a.

Additionally, the capture instructions of the response classifier 606 instruct the display medium 116a to cause a depth sensor within the camera 614 to capture depth measurements of the survey respondents 122 as they approach or depart from the display medium 116a (e.g., in feet or meters). Based on the response classifier 606, the display medium 116a causes the camera 614 and the depth sensor within the camera 614 to respectively capture video clips and depth measurements of the survey respondents 122 during presentation of the digital content item 612.

As further shown in FIG. 6A, the display medium 116a connects to or synchronizes with a coupon dispenser 618. The coupon dispenser 618 dispenses coupons for any passerby of the display medium 116a to take. When one of the survey respondents 122 takes a coupon from the coupon dispenser 618, the coupon dispenser 618 generates a coupon identifier (or accesses a pre-determined coupon identifier) to associate with the coupon taken by one of the survey respondents 122. For ease of reference, this disclosure will describe the survey respondent 122a as having taken the coupon. The coupon dispenser 618 further communicates the coupon identifier to the display medium 116a for association with the video clip of the survey respondent 122a who took the coupon.

After the biometric sensors capture the biometric data, the display medium 116a generates the data packet 620 and sends the data packet 620 to the server device(s) 102. As shown in FIG. 6A, the data packet 620 represents a type of response to the digital survey. Specifically, the data packet 620 comprises the survey identifier 604, the response classifier 606, biometric data 624 captured by the biometric sensors, and a coupon identifier 626. The data packet 620 also optionally comprises a respondent identifier 622. In some embodiments, however, the biometric survey system 104 generates the respondent identifier 622 only after applying a facial recognition algorithm to detect a presence of one or more survey respondents 122 within the video clip. Regardless of whether the data packet 620 comprises the respondent identifier 622, the respondent identifier 622 comprises a unique identifier for the survey respondent 122a who interacted with the display medium 116a and took the coupon.

As explained below with reference to FIG. 6B, the biometric survey system 104 uses the survey identifier 604 and response classifier 606 for processing the biometric data 624. The biometric data 624 includes data that represents the video clip and the depth measurement captured by the biometric sensors described above. Additionally, the coupon identifier 626 identifies the coupon taken by the survey respondent 122a.

FIG. 6B illustrates a data-flow diagram 628 that depicts the biometric survey system 104 analyzing and converting the biometric data 624 into respondent characteristics and then categorizing the respondent characteristics into a response database 638a. As shown in FIG. 6B, the biometric survey system 104 performs an act 630 of identifying a digital survey. Consistent with the disclosure above, based on the survey identifier 604, the biometric survey system 104 identifies a digital file that comprises input parameters for the digital survey and the survey identifier 604. By identifying the digital file that contains the digital survey, the biometric survey system 104 also identifies an associated response database within which to categorize information in the data packet 620.

As further shown in FIG. 6B, the biometric survey system 104 performs an act 632 of selecting biometric data analyses. Specifically, the response classifier 606 triggers the biometric survey system 104 to perform act 330 of selecting specific biometric data analyses. Here, the response classifier 606 includes instructions for the biometric survey system 104 to select facial recognition algorithms that determine an age of the survey respondent 122a, a gender of the survey respondent 122a, and a respondent-engagement level of the survey respondent 122a. Additionally, the response classifier 606 further includes instructions for the biometric survey system 104 to select an object detection algorithm that determines objects associated with the survey respondent 122a within the video clip.

Upon selecting specific biometric data analyses, the biometric survey system 104 performs an act 634 of analyzing and converting the biometric data 624 into respondent characteristics. As suggested by FIG. 6B, the biometric survey system 104 applies each of the selected biometric data analyses. The following paragraphs describe the analysis and conversion of the biometric data 624 according to each selected biometric data analysis. Although the following paragraphs describe the biometric data analyses in a numbered order, the biometric survey system 104 may perform the biometric data analyses and conversions described below simultaneously or in any order.

First, the biometric survey system 104 applies a facial recognition algorithm to the video clip and the depth measurements that determines an age of the survey respondent 122a. Specifically, the biometric survey system 104 applies HPFS to images of the survey respondent 120a from the video. Based on training the HPFS to estimate the age of faces within images, the biometric survey system 104 determines that the survey respondent 120a is between the ages of forty and forty-nine. Accordingly, the biometric survey system 104 converts the video clip of the survey respondent 122a interacting with the display medium 116a (from within the biometric data 624) into an age classification of between forty and forty-nine.

Second, the biometric survey system 104 applies a facial recognition algorithm to the video clip and the depth measurements that determines a gender of the survey respondent 122a. Specifically, the biometric survey system 104 applies a Fisherface algorithm to images of the survey respondent 122a from the video. Based on training the Fisherface algorithm to recognize male and female faces within images, the biometric survey system 104 determines that the survey respondent 122a is a female. Accordingly, the biometric survey system 104 converts the video clip of the survey respondent 122a interacting with the display medium 116a (from within the biometric data 624) into a gender classification of female.

Third, the biometric survey system 104 applies an embodiment of the engagement-level analysis to the video clip of the survey respondent 122a interacting with the display medium 116a. Specifically, the biometric survey system 104 uses a hidden Markov model to analyze the eye movement of the survey respondent 122a in the video clip. Based on the hidden Markov model, the biometric survey system 104 assigns a score to the eye-movement pattern. Here, the biometric survey system 104 assigns a score of 2.0 to the eye-movement pattern. Accordingly, the biometric survey system 104 converts the video clip from within the biometric data 624 into a respondent-engagement level of 2.0 for the survey respondent 122a.

In addition to converting the biometric data 624 into respondent characteristics of an age classification, a gender classification, and a respondent-engagement level, the biometric survey system 104 optionally performs act 636 of analyzing the biometric data 624 to identify objects associated with the survey respondent 122a. Accordingly, the biometric survey system 104 applies an object detection algorithm to the same video clip of the survey respondent 122a. For example, the biometric survey system 104 applies a version of HOG, SIFT, or SURF to the video clip to detect objects associated with the survey respondent 122a, such as objects the survey respondent 122a is carrying or wearing or objects accompanying the survey respondent 122a. As applied here, the biometric survey system 104 detects that the survey respondent 122*a* is carrying a mobile phone.

As noted above, the biometric survey system 104 optionally generates a response identifier for survey respondents only after applying a facial recognition algorithm to detect a presence of one or more survey respondents 122 within the video clip. In such embodiments, the biometric survey system 104 applies a facial recognition algorithm to video clips of one or more survey respondents 122 interacting with the display medium 116*a*. Based on the facial recognition algorithm, the biometric survey system 104 may identify more than one of the survey respondents 122 within a single video clip or one of the survey respondents 122 within multiple video clips. In such embodiments, the biometric survey system 104 generates a unique respondent identifier for each of the unique survey respondents 122 identified within one or more video clips. Additionally, when assigning respondent identifiers only after applying a facial recognition algorithm, the biometric survey system 104 performs act 634 and optionally act 636 for each of the unique survey respondents 122 identified within biometric data.

As further shown in FIG. 6B, after converting the biometric data 624 into respondent characteristics and identifying an object associated with the survey respondent 122*a*, the biometric survey system 104 categorizes the respondent characteristics and associated information within the response database 638*a*. As organized within FIG. 6B, the response database 638*a* includes a column 640*a* for respondent identifiers, a column 640*b* for survey identifiers, a column 640*c* for age classification, a column 640*d* for gender classification, a column 640*e* for respondent-engagement level, and a column 640*f* for associated objects. The biometric survey system 104 categorizes the information from data packet 620 within the first row of the response database 638*a*, including categorization of the respondent characteristics converted from the biometric data 624.

As shown in the column 640*a* of FIG. 6B, the biometric survey system 104 orders the response database 638*a* by the respondent identifiers. Specifically, the biometric survey system 104 orders information associated with each unique survey respondent 122 in descending alphabetical and numeric order by respondent identifier. As suggested above, however, the biometric survey system 104 may sort and reorder the information within the response database 638*a* according to the information within any of the columns 640*a*-640*f*. For example, in certain embodiments, the biometric survey system 104 sorts the information within the response database 638*a* in ascending or descending order according to the age classifications shown in column 640*e*.

For purposes of simplicity, FIG. 6B illustrates the response database 638*a* with five rows of information extracted or converted from two of more data packets. In some embodiments, however, the biometric survey system 104 categorizes information extracted or converted from any number of data packets that include biometric data—with respondent characteristics for each unique survey respondent—within a response database. For example, in some embodiments, a response database includes information associated with different digital content items presented on a single display medium. Although not shown, the response database 638*a* of FIG. 6B includes additional rows of information extracted or converted from additional data packets.

In addition to categorizing and sorting a response database, in some embodiments, the biometric survey system 104 updates the response database upon receiving additional information. For example, the biometric survey system 104 may update a response database upon receiving newly converted respondent characteristics or information concerning a transaction. FIG. 6C illustrates a response database that the biometric survey system 104 updates based on newly received information.

As shown in FIG. 6C, the biometric survey system 104 performs an act 642 of receiving a transaction notice and an act 644 of determining a coupon expired. In particular, the biometric survey system 104 receives a notice from a point-of-sale system that a first coupon taken by the survey respondent 122*a* (and associated with the coupon identifier 626) has been redeemed. Additionally, the biometric survey system 104 determines that a second coupon and a third coupon have expired based on expiration dates associated with additional coupon identifiers. The second and third coupons were taken by survey respondents assigned different respondent identifiers, as shown in the second and fifth row of the response database 638*a* of FIG. 6B.

Based on receiving the transaction notice for the first coupon, the biometric survey system 104 updates the response database 638*a*. As shown in FIG. 6C, a response database 638*b* represents an updated version of the response database 638*a*. In addition to the columns 640*a*-640*f*, the response database 638*b* now includes a column 640*h* for transactional information. As indicated in the first row of the response database 638*b*, the biometric survey system 104 identifies that the coupon taken by the survey respondent 122*a* has been redeemed in a transaction. Here, the identification in the first row of the column 640*h* is marked with the word "Redeemed." Any other suitable identification, however, may be used. By categorizing the identification of the transaction within the first row of information associated with the survey respondent 122*a*, the biometric survey system 104 likewise associates the coupon identifier 626 and the identification of the transaction with the respondent characteristics of the survey respondent 122*a*.

Conversely, based on determining that the second and third coupons expired, the biometric survey system 104 indicates within the response database 638 that the coupons taken by the additional survey respondents have expired. Here, the indications in the second and fifth rows of the column 640*h* are marked with the word "Expired." Any other suitable indication, however, may be used. By categorizing the indications within the second and fifth rows of information associated with the additional survey respondents, the biometric survey system 104 likewise associates coupon identifiers and the indications of no corresponding transactions with the respondent characteristics of the additional survey respondents.

As noted above, in addition to creating a response database and categorizing respondent characteristics within the database, in some embodiments, the biometric survey system 104 generates reports that comprise information about survey respondents who interacted with certain display mediums. In some such embodiments, for instance, the report identifies specific respondent characteristics that correspond to survey respondents who interacted with digital content items presented on a display medium.

Figure 7:
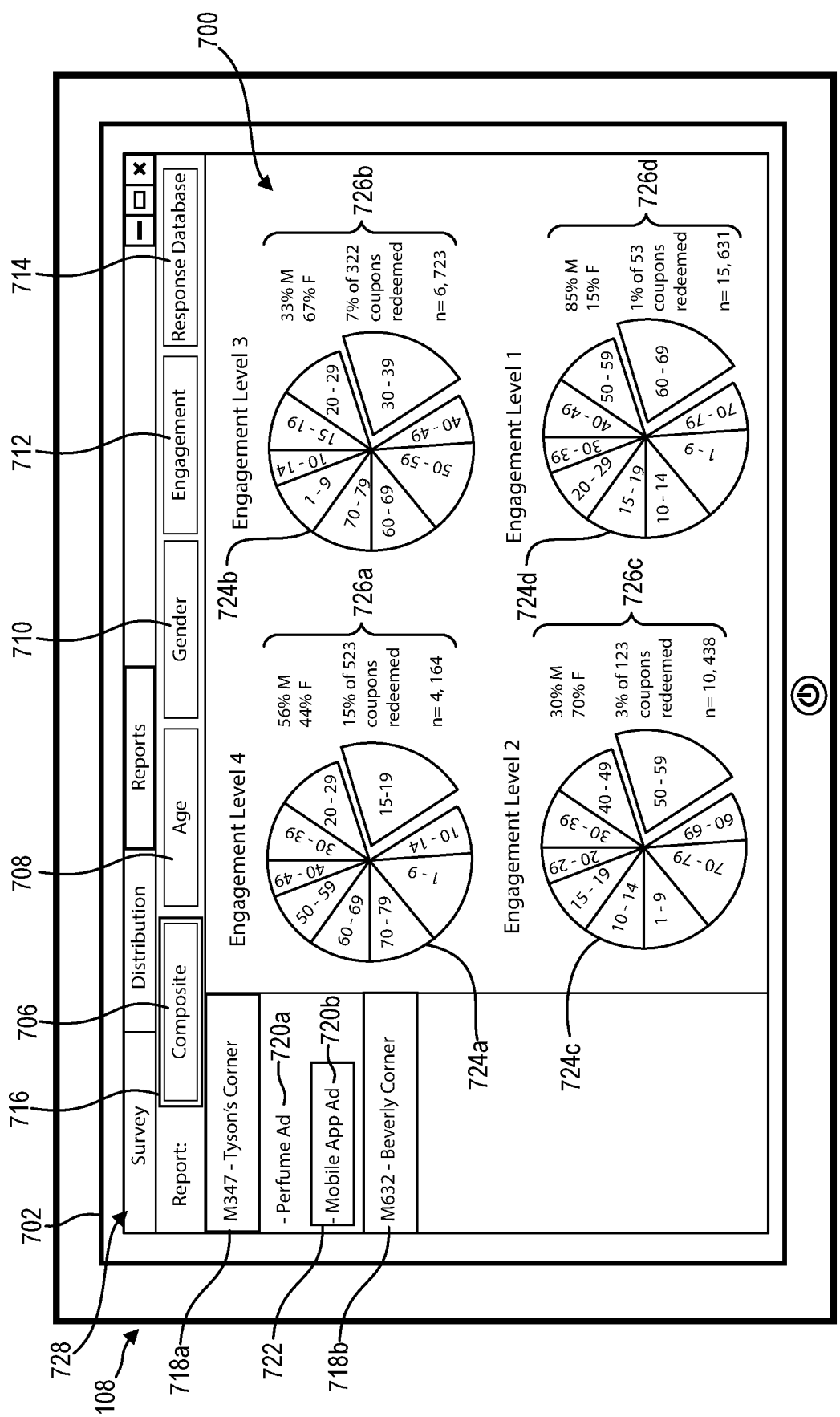
FIG. 7 illustrates a respondent-characteristic report in accordance with one or more embodiments.

FIG. 7 illustrates an embodiment of a respondent-characteristic report for the display medium 116*a* generated by the biometric survey system 104. As shown in FIG. 7, the biometric survey system 104 provides a respondent-characteristic report 700 for display within a graphical user interface 728. A screen 702 of the administrator device 108 in turn presents the respondent-characteristic report 700 for the survey administrator 106.

As suggested by FIG. 7, the respondent-characteristic report 700 may include information related to different display mediums from different locations. Reflecting such different display mediums, the respondent-characteristic report 700 includes a first location thumbnail 718a and a second location thumbnail 718b. The first location thumbnail 718a corresponds to the display medium 116a located at a first location. The second location thumbnail 718b corresponds to a display medium located at a second location.

Consistent with the disclosure above, display mediums at different locations may present different digital content items and/or the same digital content items. As suggested by FIG. 7, the display medium 116a presents different digital content items. The respondent-characteristic report 700 includes a first content-item thumbnail 720a and a second content-item thumbnail 720b. The first content-item thumbnail 720a and the second content-item thumbnail 720b respectively correspond to the digital content item 612 and an additional digital content item presented by the display medium 116a.

When, as here, display mediums present different digital content items, a respondent-characteristic report may include respondent characteristics corresponding to survey respondents who interacted with different digital content items at different locations and/or the same digital content items at different locations. As shown in FIG. 7, a content-item indicator 722 surrounds the first content-item thumbnail 720a to indicate that the data represented within the respondent-characteristic report 700 corresponds to the survey respondents 122 who interacted with the digital content item 612. Conversely, when the content-item indicator 722 surrounds the second content-item thumbnail 720b, the data represented within the respondent-characteristic report 700 corresponds to the survey respondents 122 who interacted with the additional digital content item.

As further shown in FIG. 7, the respondent-characteristic report 700 includes a first respondent-engagement-level chart 724a, a second respondent-engagement-level chart 724b, a third respondent-engagement-level chart 724c, and a fourth respondent-engagement-level chart 724d. Each of the charts 724a, 724b, 724c, and 724d include a graphical representation of respondent characteristics exhibited by the survey respondents 122 who interacted with the digital content item 612. Specifically, the charts 724a-724d represent the survey respondents 122 who exhibited different respondent-engagement levels while interacting with the digital content item 612—along with their accompanying age classifications. As shown, the charts 724a, 724b, 724c, and 724d respectively represent the survey respondents 122 who exhibited a respondent-engagement level of four, three, two, and one—with four representing the highest respondent-engagement level and one representing the lowest respondent-engagement level. Moreover, the charts 724a, 724b, 724c, and 724d also respectively represent age classifications for the survey respondents 122 who exhibited a respondent-engagement level of four, three, two, and one. Specifically, each of the charts 724a, 724b, 724c, and 724d includes a graphical representation of age classifications of 1-9, 10-14, 15-19, 20-29, 30-39, 40-49, 50-59, 60-69, 70-79, for each group of the survey respondents 122 who exhibited a particular respondent-engagement level.

The respondent-characteristic report 700 further includes data associated with each of the charts 724a, 724b, 724c, and 724d that indicate a distribution of additional respondent characteristics and other tracked information. Specifically, the respondent-characteristic report 700 includes respondent statistics 726a, respondent statistics 726b, respondent statistics 726c, and respondent statistic 726d. Each of the respondent statistics 726a, 726b, 726c, and 726d include a number of survey respondents, percentage of males and females, and a percentage of redeemed coupons of coupons taken for the survey respondents 122 represented by the charts 724a, 724b, 724c, and 724d.

For example, the respondent statistics 726a indicate that a certain number of survey respondents (4,164) exhibited a respondent-engagement level of four while interacting with the digital content item 612. The respondent statistics 726a further indicate that a certain percentage of the survey respondents 122 who exhibited a respondent-engagement level of four are male (56%) and female (44%). Moreover, the respondent statistics 726a also indicate that a certain percentage of coupons (15%) taken by the survey respondents 122 who exhibited a respondent-engagement level of four were redeemed out of a certain number of coupons taken (523). The respondent statistics 726b, 726c, and 726d include similar statistics for their respective groups of the survey respondents 122.

As suggested by FIG. 7, the respondent-characteristic report 700 reports respondent characteristics determined by the biometric survey system 104. By converting biometric data into respondent characteristics, as described in FIG. 6B, the biometric survey system 104 determines that survey respondents exhibited the respondent characteristics shown within the charts 724a-724d and the respondent statistics 726a-726b—while the display medium 116a presented the digital content item 612.

In addition to generating respondent-characteristic reports for survey respondents who interacted with the same digital content item, the biometric survey system 104 provides selectable options to generate a respondent-characteristic report showing different respondent characteristics in isolation. As shown in FIG. 7, for example, the respondent-characteristic report 700 includes a composite-report option 706, an age-classification-report option 708, a gender-classification-report option 710, and an engagement-level-report option 712. A report indicator 716 surrounds the composite-report option 706 to indicate that the respondent-characteristic report 700 currently includes a composite of different respondent characteristics.

When the biometric survey system 104 receives an indication that the survey administrator 106 selects the age-classification-report option 708, the gender-classification-report option 710, or the engagement-level-report option 712, however, the biometric survey system 104 updates the respondent-characteristic report 700 to include data corresponding to an age classification, gender classification, or respondent-engagement level, respectively. In each case, however, the updated respondent-characteristic report shows data representing a single respondent characteristic. For example, the age-classification-report option 708 triggers the biometric survey system 104 to update the respondent-characteristic report 700 to include an age classification for the survey respondents 122 who interacted with the digital content item 612 without the respondent characteristics of gender classification or respondent-engagement level.

Additionally, and as indicated above, the biometric survey system 104 optionally generates a report that depicts a response database for a digital survey. As shown in FIG. 7, for example, the respondent-characteristic report 700 includes a response-database-report option 714. When the biometric survey system 104 receives an indication that the survey administrator 106 selects the response-database-report option 714, the biometric survey system 104 generates a report showing a response database that categorizes the underlying response data for a digital survey. For example, upon receiving an indication that the survey administrator 106 selects the response-database-report option 714, the biometric survey system 104 optionally generates a respondent-characteristic report with a graphical representation of the response database 638b of FIG. 6C.

Figure 8:
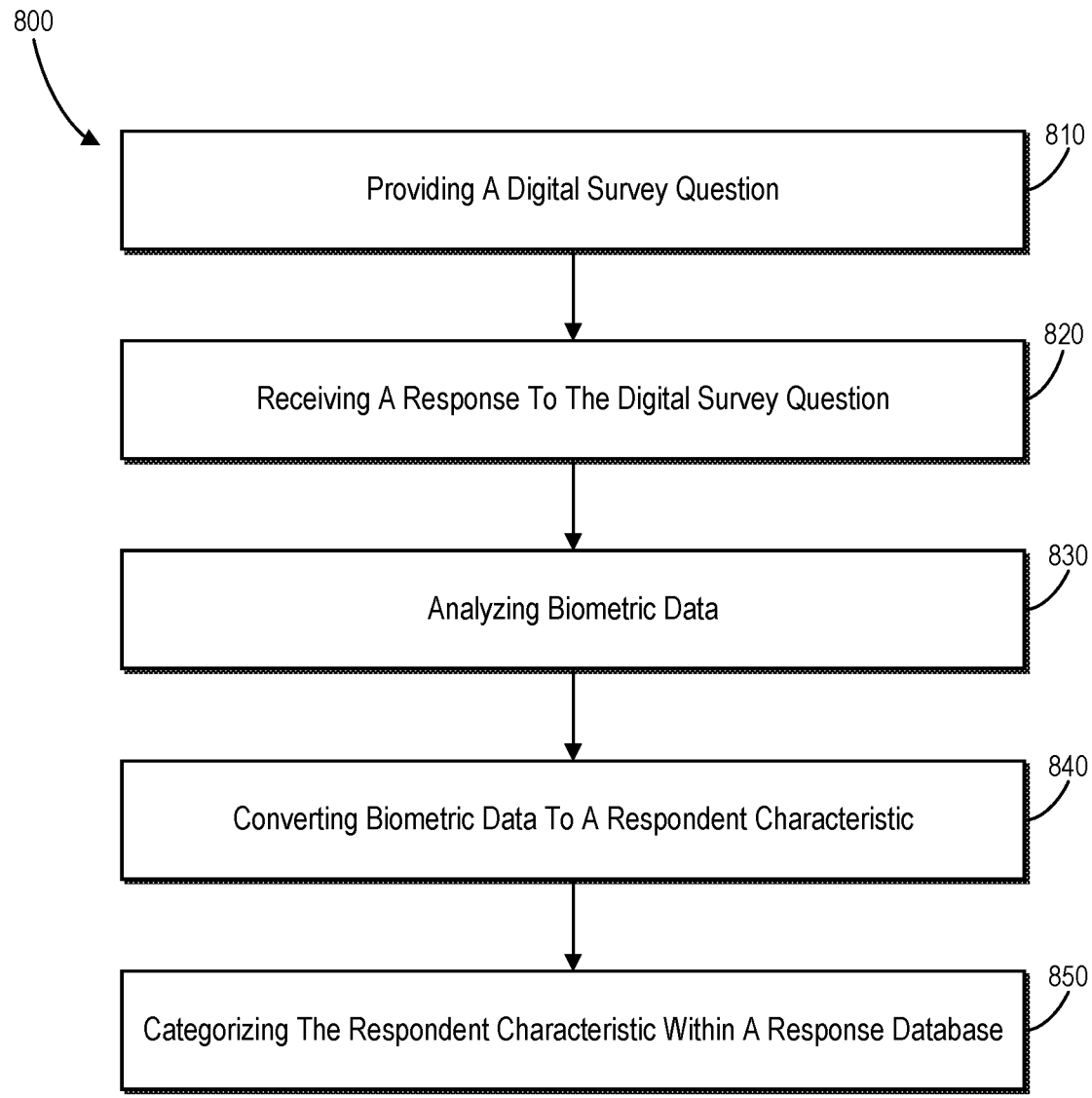
FIG. 8 illustrates a flowchart of a series of acts in a method of collecting and converting biometric data into respondent characteristics based on responses to a digital survey question in accordance with one or more embodiments.

Turning now to FIG. 8, this figure illustrates a flowchart of a series of acts in a method 800 of collecting and converting biometric data into respondent characteristics based on responses to a digital survey question. While FIG. 8 illustrates acts according to one embodiment, alternative embodiments may omit, add to, reorder, and/or modify any of the acts shown in FIG. 8.

As shown in FIG. 8, the method 800 includes an act 810 of providing a digital survey question. In particular, act 810 includes providing, to a client device, a digital survey question as part of a digital survey, the digital survey question comprising a textual query and a biometric query. In one or more embodiments, providing the digital survey question as part of the digital survey comprises providing the digital survey question comprising the textual query, the biometric query, and a question identifier.

As further shown in FIG. 8, the method 800 includes an act 820 of receiving a response to the digital survey question. In particular, act 820 includes receiving, from the client device, a response to the digital survey question comprising a reply to the textual query and biometric data captured by a biometric sensor in response to the biometric query. In one or more embodiments, receiving the response to the digital survey question comprising the reply to the textual query and the biometric data captured in response to the biometric query comprises receiving a data packet that comprises the reply, the biometric data, and the question identifier.

Similarly, in one or more embodiments, receiving the response to the digital survey question comprising the reply to the textual query and biometric data captured in response to the biometric query comprises receiving one or more of a blood pressure, breath rate, heart rate, image, video, and audio file as part of the biometric data captured in response to the biometric query.

As further shown in FIG. 8, the method 800 includes an act 830 of analyzing biometric data 830. In one or more embodiments, analyzing the biometric data comprises, based on the question identifier, selecting a biometric-data analysis corresponding to at least one respondent characteristic.

As further shown in FIG. 8, the method 800 includes an act 840 of converting the biometric data to a respondent characteristic. In particular, act 840 includes, based on analyzing the biometric data, converting the biometric data to a respondent characteristic.

In some embodiments, converting the biometric data to the respondent characteristic comprises converting the biometric data to a respondent emotion associated with the reply to the textual query. For example, in certain embodiments, converting the biometric data to the respondent emotion associated with the reply to the textual query comprises converting the biometric data to one of a positive emotion, a neutral emotion, or a negative emotion, or to one of a strong emotion, a moderate emotion, or a weak emotion.

Additionally, in some embodiments, converting the biometric data to the respondent characteristic comprises converting the biometric data to a respondent-engagement level associated with the reply to the textual query. For example, in certain embodiments, converting the biometric data to the respondent-engagement level associated with the reply to the textual query is based on an action performed by the respondent while the client device presents the textual query.

Similarly, in some embodiments, converting the biometric data to the respondent characteristic comprises converting the biometric data to one or more biographic classifications of the respondent. For example, in certain embodiments, converting the biometric data to the one or more biographic classifications of the respondent comprises converting the biometric data to one or more of an age classification, a gender classification, and a race classification.

As further shown in FIG. 8, the method 800 includes an act 850 of categorizing the respondent characteristic within a response database. In particular, act 850 includes categorizing the respondent characteristic within a response database of the digital survey.

Figure 9:
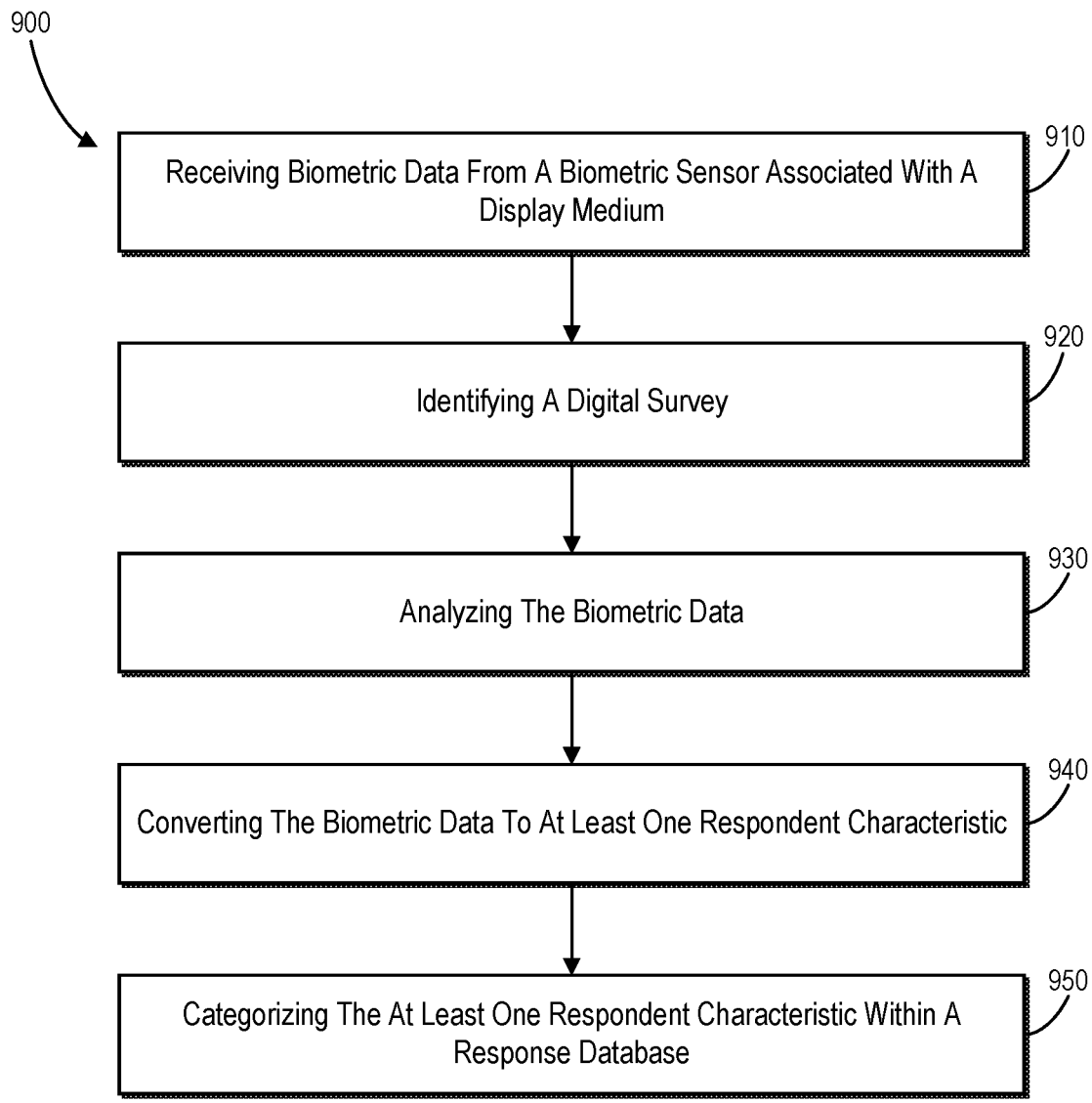
FIG. 9 illustrates a flowchart of a series of acts in a method of collecting and converting biometric data into characteristics of respondents who interact with a display medium in accordance with one or more embodiments.

Turning now to FIG. 9, this figure illustrates a flowchart of a series of acts in a method 900 of collecting and converting biometric data into respondent characteristics of respondents who interact with a display medium. While FIG. 9 illustrates acts according to one embodiment, alternative embodiments may omit, add to, reorder, and/or modify any of the acts shown in FIG. 9.

As shown in FIG. 9, the method 900 includes an act 910 of receiving biometric data from a biometric sensor associated with a display medium. In particular, act 910 can include receiving, by the one or more servers, biometric data from a biometric sensor associated with a display medium, the biometric data associated with a survey identifier and corresponding to at least one respondent that interacted with the display medium.

For example, in some embodiments, receiving the biometric data from the biometric sensor associated with the display medium comprises receiving a data packet that comprises the biometric data, the survey identifier, the response classifier, and a respondent identifier, the survey identifier corresponding to a physical location of the display medium. In some such embodiments, receiving the biometric data from the biometric sensor associated with the display medium comprises receiving an image from a camera; and analyzing the biometric data comprises analyzing the biometric data to identify the at least one respondent and at least one object associated with the at least one respondent.

Similarly, in some embodiments, analyzing the biometric data to identify the at least one respondent and the at least one object associated with the at least one respondent comprises analyzing the biometric data to identify the at least one respondent and one of a person, a product, or an accessory as the at least one object. In some such embodiments, receiving the biometric data from the biometric sensor associated with the display medium comprises receiving the biometric data corresponding to a plurality of respondents that interacted with the display medium, the biometric data comprising a biometric-data packet for each of the plurality of respondents and the plurality of respondents comprising a first respondent and a second respondent; analyzing the biometric data comprises analyzing the biometric data corresponding to the plurality of respondents; converting the biometric data to the at least one respondent characteristic associated with the at least one respondent comprises converting each biometric-data packet to a respondent characteristic associated with each of the plurality of respondents, the respondent characteristic associated with each of the plurality of respondents comprising a first respondent characteristic associated with the first respondent and a second respondent characteristic associated with the second respondent; and categorizing the at least one respondent characteristic within the response database of the digital survey comprises categorizing each respondent characteristic within the response database of the digital survey.

As noted above, in some embodiments, the biometric survey system 104 tracks coupons. Accordingly, in some embodiments, the method 900 further comprises receiving a first coupon identifier corresponding to a first coupon taken by the first respondent and a second coupon identifier corresponding to a second coupon taken by the second respondent; based on the first coupon identifier, receiving a notice that the first coupon was redeemed as part of a transaction; and based on the second coupon identifier, determining that the second coupon expired without a corresponding transaction. Relatedly, in some embodiments, the method 900 further comprises associating the first coupon identifier and an identification of the transaction with the first respondent characteristic within the response database; and associating the second coupon identifier and an indication of no corresponding transaction with the second respondent characteristic within the response database.

As further shown in FIG. 9, the method 900 includes an act 920 of identifying a digital survey. In particular, act 920 can include, based on the survey identifier, identifying a digital survey.

Additionally, and as also shown in FIG. 9, the method 900 includes an act 930 of analyzing the biometric data. In particular, act 930 can include, based on the survey identifier or a response classifier, analyzing the biometric data.

Moreover, as shown in FIG. 9, the method 900 includes an act 940 of converting the biometric data to at least one respondent characteristic. In particular, act 940 can include, based on analyzing the biometric data, converting the biometric data to at least one respondent characteristic associated with the at least one respondent.

As further shown in FIG. 9, the method 900 includes an act 950 of categorizing the at least one respondent characteristic within a response database. In particular, act 950 can include categorizing the at least one respondent characteristic within a response database of the digital survey.

In addition to the acts 910-950, in some embodiments, the method 900 further comprises identifying a number of the plurality of respondents that interacted with the display medium. Additionally, in some embodiments of method 900, receiving the biometric data from the biometric sensor associated with the display medium comprises receiving the biometric data corresponding to a first respondent and biometric data corresponding to a second respondent; analyzing the biometric data comprises analyzing the biometric data corresponding to the first respondent and analyzing the biometric data corresponding to the second respondent; converting the biometric data to the at least one respondent characteristic associated with the at least one respondent comprises converting the biometric data corresponding to the first respondent to a first respondent characteristic associated with the first respondent and converting the biometric data corresponding to the second respondent to a second respondent characteristic associated with the second respondent; and categorizing the at least one respondent characteristic within the response database of the digital survey comprises categorizing the first respondent characteristic and the second respondent characteristic within the response database of the digital survey.

Figure 10:
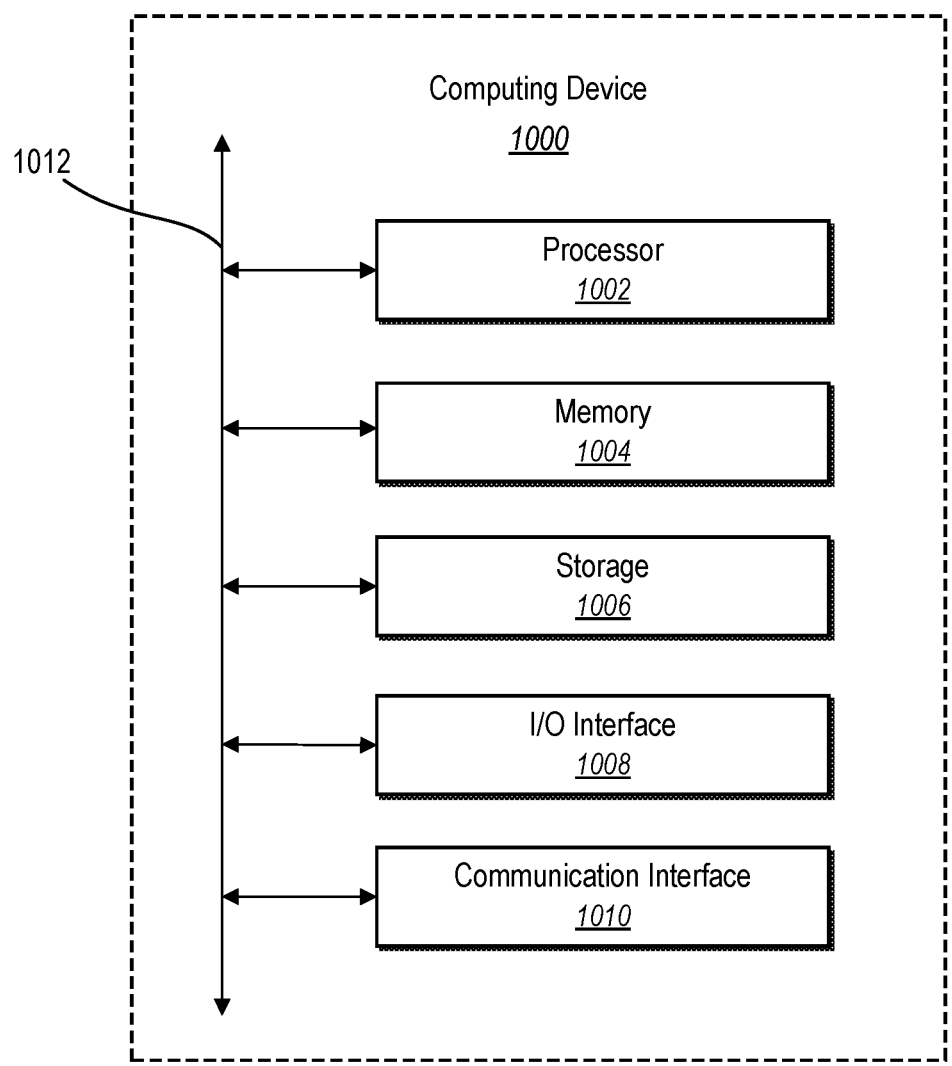
FIG. 10 illustrates a block diagram of a computing device in accordance with one or more embodiments.

FIG. 10 illustrates a block diagram of an exemplary computing device 1000 that may be configured to perform one or more of the processes described above. One will appreciate that one or more computing devices such as the computing device 1000 may implement the server device(s) 116 and/or other devices described above in connection with FIG. 1. As shown by FIG. 10, the computing device 1000 can comprise a processor 1002, a memory 1004, a storage device 1006, an I/O interface 1008, and a communication interface 1010, which may be communicatively coupled by way of a communication infrastructure 1012. While the exemplary computing device 1000 is shown in FIG. 10, the components illustrated in FIG. 10 are not intended to be limiting. Additional or alternative components may be used in other embodiments. Furthermore, in certain embodiments, the computing device 1000 can include fewer components than those shown in FIG. 10. Components of the computing device 1000 shown in FIG. 10 will now be described in additional detail.

In one or more embodiments, the processor 1002 includes hardware for executing instructions, such as those making up a computer program. As an example and not by way of limitation, to execute instructions, the processor 1002 may retrieve (or fetch) the instructions from an internal register, an internal cache, the memory 1004, or the storage device 1006 and decode and execute them. In one or more embodiments, the processor 1002 may include one or more internal caches for data, instructions, or addresses. As an example and not by way of limitation, the processor 1002 may include one or more instruction caches, one or more data caches, and one or more translation lookaside buffers ("TLBs"). Instructions in the instruction caches may be copies of instructions in the memory 1004 or the storage device 1006.

The memory 1004 may be used for storing data, metadata, and programs for execution by the processor(s). The memory 1004 may include one or more of volatile and non-volatile memories, such as Random Access Memory ("RAM"), Read Only Memory ("ROM"), a solid state disk ("SSD"), Flash, Phase Change Memory ("PCM"), or other types of data storage. The memory 1004 may be internal or distributed memory.

The storage device 1006 includes storage for storing data or instructions. As an example and not by way of limitation, storage device 1006 can comprise a non-transitory storage medium described above. The storage device 1006 may include a hard disk drive ("HDD"), a floppy disk drive, flash memory, an optical disc, a magneto-optical disc, magnetic tape, or a Universal Serial Bus ("USB") drive or a combination of two or more of these. The storage device 1006 may include removable or non-removable (or fixed) media, where appropriate. The storage device 1006 may be internal or external to the computing device 1000. In one or more embodiments, the storage device 1006 is non-volatile, solid-state memory. In other embodiments, the storage device 1006 includes read-only memory ("ROM"). Where appropriate, this ROM may be mask programmed ROM, programmable ROM ("PROM"), erasable PROM ("EPROM"), electrically erasable PROM ("EEPROM"), electrically alterable ROM ("EAROM"), or flash memory or a combination of two or more of these.

The I/O interface 1008 allows a user to provide input to, receive output from, and otherwise transfer data to and receive data from the computing device 1000. The I/O interface 1008 may include a mouse, a keypad or a keyboard, a touch screen, a camera, an optical scanner, network interface, modem, other known I/O devices or a combination of such I/O interfaces. The I/O interface 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 1008 is configured to provide graphical data to a display for presentation to a user. The graphical data may be representative of one or more graphical user interfaces and/or any other graphical content as may serve a particular implementation.

The communication interface 1010 can include hardware, software, or both. In any event, the communication interface 1010 can provide one or more interfaces for communication (such as, for example, packet-based communication) between the computing device 1000 and one or more other computing devices or networks. As an example and not by way of limitation, the communication interface 1010 may include a network interface controller ("NIC") or network adapter for communicating with an Ethernet or other wire-based network or a wireless NIC ("WNIC") or wireless adapter for communicating with a wireless network, such as a WI-FI.

Additionally, or alternatively, the communication interface 1010 may facilitate communications with an ad hoc network, a personal area network ("PAN"), a local area network ("LAN"), a wide area network ("WAN"), a metropolitan area network ("MAN"), or one or more portions of the Internet or a combination of two or more of these. One or more portions of one or more of these networks may be wired or wireless. As an example, the communication interface 1010 may facilitate communications with a wireless PAN ("WPAN") (such as, for example, a BLUETOOTH WPAN), a WI-FI network, a WI-MAX network, a cellular telephone network (such as, for example, a Global System for Mobile Communications ("GSM") network), or other suitable wireless network or a combination thereof.

Additionally, the communication interface 1010 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 1012 may include hardware, software, or both that couples components of the computing device 1000 to each other. As an example and not by way of limitation, the communication infrastructure 1012 may include an Accelerated Graphics Port ("AGP") or other graphics bus, an Enhanced Industry Standard Architecture ("EISA") bus, a front-side bus ("FSB"), a HYPERTRANSPORT ("HT") interconnect, an Industry Standard Architecture ("ISA") bus, an INFINIBAND interconnect, a low-pin-count ("LPC") bus, a memory bus, a Micro Channel Architecture ("MCA") bus, a Peripheral Component Interconnect ("PCI") bus, a PCI-Express ("PCIe") bus, a serial advanced technology attachment ("SATA") bus, a Video Electronics Standards Association local ("VLB") bus, or another suitable bus or a combination thereof.

Figure 11:
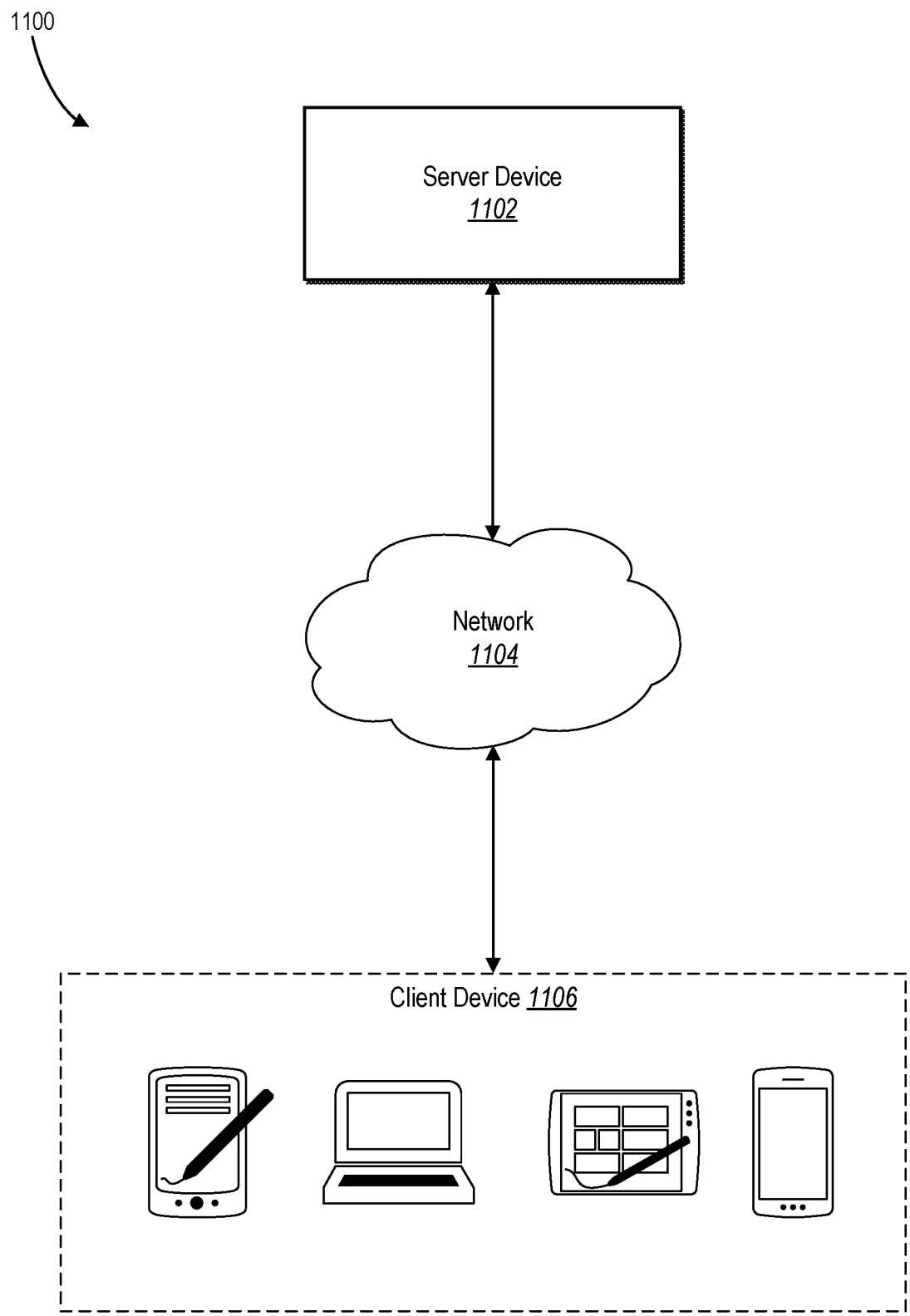
FIG. 11 illustrates a networking environment of a biometric survey system in accordance with one or more embodiments.

FIG. 11 illustrates an example network environment 1100 of the communication system 100. Network environment 1100 includes a client device 1106, and a server device 1102 connected to each other by a network 1104. Although FIG. 11 illustrates a particular arrangement of client device 1106, server device 1102, and network 1104, this disclosure contemplates any suitable arrangement of client device 1106, server device 1102, and network 1104. As an example and not by way of limitation, two or more of client device 1106, and server device 1102 may be connected to each other directly, bypassing network 1104. As another example, two or more of client device 1106 and server device 1102 may be physically or logically co-located with each other in whole, or in part. Moreover, although FIG. 11 illustrates a particular number of client devices 1106, server devices 1102, and networks 1104, this disclosure contemplates any suitable number of client devices 1106, server devices 1102, and networks 1104. As an example and not by way of limitation, network environment 1100 may include multiple client devices 1106, server devices 1102, and networks 1104.

This disclosure contemplates any suitable network 1104. As an example and not by way of limitation, one or more portions of network 1104 may include an ad hoc network, an intranet, an extranet, a virtual private network ("VPN"), a local area network ("LAN"), a wireless LAN ("WLAN"), a wide area network ("WAN"), a wireless WAN ("WWAN"), a metropolitan area network ("MAN"), a portion of the Internet, a portion of the Public Switched Telephone Network ("PSTN"), a cellular telephone network, or a combination of two or more of these. Network 1104 may include one or more networks 1104.

Links may connect client device 1106, and server device 1102 to communication network 1104 or to each other. This disclosure contemplates any suitable links. In particular embodiments, one or more links include one or more wireline (such as for example Digital Subscriber Line ("DSL") or Data Over Cable Service Interface Specification ("DOCSIS")), wireless (such as for example Wi-Fi or Worldwide Interoperability for Microwave Access ("WiMAX")), or optical (such as for example Synchronous Optical Network (SONET) or Synchronous Digital Hierarchy ("SDH")) links. In particular embodiments, one or more links each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link, or a combination of two or more such links. Links need not necessarily be the same throughout network environment 1100. One or more first links may differ in one or more respects from one or more second links.

In particular embodiments, client device 1106 may be an electronic device including hardware, software, or embedded logic components or a combination of two or more such components and capable of carrying out the appropriate functionalities implemented or supported by client device 1106. As an example and not by way of limitation, a client device 1106 may include any of the computing devices discussed above in relation to FIG. 11. A client device 1106 may enable a network user at client device 1106 to access network 1104.

In particular embodiments, client device 1106 may include a web browser, such as MICROSOFT INTERNET EXPLORER, GOOGLE CHROME, or MOZILLA FIREFOX, and may have one or more add-ons, plug-ins, or other extensions, such as TOOLBAR or YAHOO TOOLBAR. A user at client device 1106 may enter a Uniform Resource Locator ("URL") or other address directing the web browser to a particular server (such as server, or a server associated with a third-party system), and the web browser may generate a Hyper Text Transfer Protocol ("HTTP") request and communicate the HTTP request to server. The server may accept the HTTP request and communicate to client device 1106 one or more Hyper Text Markup Language ("HTML") files responsive to the HTTP request. Client device 1106 may render a webpage based on the HTML files from the server for presentation to the user. This disclosure contemplates any suitable webpage files. As an example and not by way of limitation, webpages may render from HTML files, Extensible Hyper Text Markup Language ("XHTML") files, or Extensible Markup Language ("XML") files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, server device 1102 may include a variety of servers, sub-systems, programs, modules, logs, and data stores. In particular embodiments, server device 1102 may include one or more of the following: a web server, action logger, API-request server, relevance-and-ranking engine, content-object classifier, notification controller, action log, third-party-content-object-exposure log, inference module, authorization/privacy server, search module, advertisement-targeting module, user-interface module, user-profile store, connection store, third-party content store, or location store. Server device 1102 may also include suitable components such as network interfaces, security mechanisms, load balancers, failover servers, management-and-network-operations consoles, other suitable components, or any suitable combination thereof.

In particular embodiments, server device 1102 may include one or more user-profile stores for storing user profiles. A user profile may include, for example, biographic information, demographic information, behavioral information, social information, or other types of descriptive information, such as work experience, educational history, hobbies or preferences, interests, affinities, or location. Interest information may include interests related to one or more categories. Categories may be general or specific. Additionally, a user profile may include financial and billing information of users (e.g., survey respondents 108, customers, etc.).

The foregoing specification is described with reference to specific exemplary embodiments thereof. Various embodiments and aspects of the disclosure are described with reference to details discussed herein, and the accompanying drawings illustrate the various embodiments. The description above and drawings are illustrative and are not to be construed as limiting. Numerous specific details are described to provide a thorough understanding of various embodiments.

The additional or alternative embodiments may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method comprising:
   determining a biometric query corresponding with a publicly exhibited display medium, the biometric query comprising computer-executable instructions that cause a biometric sensor of the publicly exhibited display medium to capture a specific type of biometric data;
   in response to at least one respondent interaction with the publicly exhibited display medium, causing the biometric sensor to capture a video within a first data packet;
   generating an automatic response in response to receiving the first data packet by:
      receiving, by one or more servers, the video within the first data packet from the biometric sensor associated with the publicly exhibited display medium;
      analyzing, utilizing a biometric-data analysis, the video within the first data packet to identify the specific type of biometric data and to identify a physical characteristic of the at least one respondent interaction;
      converting the specific type of biometric data from the analysis performed on the video within the first data packet to at least one respondent characteristic associated with the at least one respondent interaction;
      identifying a digital survey within a survey database based on a survey identifier associated with the physical characteristic and the specific type of biometric data within the first data packet; and
      generating, utilizing the physical characteristic and the specific type of biometric data, the automatic response to the identified digital survey within the survey database; and
   categorizing the at least one respondent characteristic and the automatic response within a response database of the digital survey.

2. The method of claim 1, further comprising providing, for display within a graphical user interface of an administrator device, a respondent-characteristic report comprising graphical representations of the at least one respondent characteristic.

3. The method of claim 1, wherein the biometric data comprises one or more of a blood pressure, breath rate, heart rate, image, video, or audio file.

4. The method of claim 1, wherein receiving the biometric data comprises receiving the first data packet that comprises the biometric data, the survey identifier, and a response classifier.

5. The method of claim 1, further comprising analyzing the biometric data using an analysis identified with a response classifier associated with the biometric data.

6. The method of claim 1, wherein converting the biometric data to the at least one respondent characteristic comprises converting the biometric data to one of a positive emotion, a neutral emotion, or a negative emotion, or to one of a strong emotion, a moderate emotion, or a weak emotion.

7. The method of claim 1, wherein converting the biometric data to the at least one respondent characteristic comprises converting the biometric data to a respondent-engagement level associated with the publicly exhibited display medium.

8. The method of claim 7, wherein the respondent-engagement level associated with the publicly exhibited display medium is based in part on an action performed by at least one respondent while interacting with the publicly exhibited display medium.

9. The method of claim 1, wherein converting the biometric data to the at least one respondent characteristic comprises converting the biometric data to one or more biographic classifications corresponding to at least one respondent.

10. A system comprising:
at least one processor; and
at least one non-transitory computer readable storage medium storing instructions that, when executed by the at least one processor, cause the system to:
determine a biometric query corresponding with a publicly exhibited display medium, the biometric query comprising computer-executable instructions that cause a biometric sensor of the publicly exhibited display medium to capture a specific type of biometric data;
in response to at least one respondent interaction with the publicly exhibited display medium, cause the biometric sensor to capture a video within a first data packet;
generate an automatic response in response to receiving the first data packet by:
receiving the video within the first data packet from the biometric sensor associated with the publicly exhibited display medium;
analyzing, utilizing a biometric-data analysis, the video within the first data packet to identify the specific type of biometric data and to identify a physical characteristic of the at least one respondent interaction;
converting the specific type of biometric data from the analysis performed on the video within the first data packet to at least one respondent characteristic associated with the at least one respondent interaction;
identifying a digital survey within a survey database based on a survey identifier associated with the physical characteristic and the specific type of biometric data within the first data packet; and
generating, utilizing the physical characteristic and the specific type of biometric data, the automatic response to the identified digital survey within the survey database; and
categorize the at least one respondent characteristic and the automatic response within a response database of the digital survey.

11. The system of claim 10, further comprising instructions that, when executed by the at least one processor, cause the system to provide, for display within a graphical user interface of an administrator device, a respondent-characteristic report comprising graphical representations of the at least one respondent characteristic.

12. The system of claim 10, wherein receiving the biometric data comprises receiving a data packet that comprises the biometric data, the survey identifier, and a response classifier that indicates an analysis to perform on the biometric data.

13. The system of claim 12, further comprising instructions that, when executed by the at least one processor, cause the system to analyze the biometric data using the analysis indicated by the response classifier.

14. The system of claim 10, wherein converting the biometric data to the at least one respondent characteristic comprises converting the biometric data to one of a positive emotion, a neutral emotion, or a negative emotion, or to one of a strong emotion, a moderate emotion, or a weak emotion.

15. The system of claim 10, wherein converting the biometric data to the at least one respondent characteristic comprises converting the biometric data to a respondent-engagement level associated with the publicly exhibited display medium.

16. A non-transitory computer-readable medium storing instructions that, when executed by at least one processor, cause a computing device to:
determine a biometric query corresponding with a publicly exhibited display medium, the biometric query comprising computer-executable instructions that cause a biometric sensor of the publicly exhibited display medium to capture a specific type of biometric data;
in response to at least one respondent interaction with the publicly exhibited display medium, cause the biometric sensor to capture a video within a first data packet;
generate an automatic response in response to receiving the first data packet by:
receiving the video within the first data packet from the biometric sensor associated with the publicly exhibited display medium;
analyzing, utilizing a biometric-data analysis, the video within the first data packet to identify the specific type of biometric data and to identify a physical characteristic of the at least one respondent interaction;
converting the specific type of biometric data from the analysis performed on the video within the first data packet to at least one respondent characteristic associated with the at least one respondent interaction;
identifying a digital survey within a survey database based on a survey identifier associated with the physical characteristic and the specific type of biometric data within the first data packet; and
generating, utilizing the physical characteristic and the specific type of biometric data, the automatic response to the identified digital survey within the survey database; and
categorize the at least one respondent characteristic and the automatic response within a response database of the digital survey.

17. The non-transitory computer-readable medium of claim 10, further comprising instructions that, when executed by the at least one processor, cause the computing device to provide, for display within a graphical user interface of an administrator device, a respondent-characteristic report comprising graphical representations of the at least one respondent characteristic.

18. The non-transitory computer-readable medium of claim 16, wherein receiving the biometric data comprises receiving the first data packet that comprises the biometric data, the survey identifier, and a response classifier that indicates an analysis to perform on the biometric data.

19. The non-transitory computer-readable medium of claim 18, further comprising instructions that, when executed by at least one processor, cause the computing device to analyze the biometric data using the analysis indicated by the response classifier.

20. The non-transitory computer-readable medium of claim 16, further comprising instructions that, when executed by at least one processor, cause the computing device to convert the biometric data to one or more biographic classifications corresponding to the at least one respondent.

\* \* \* \* \*